(12) United States Patent
Sandstrom

(10) Patent No.: US 7,522,271 B2
(45) Date of Patent: *Apr. 21, 2009

(54) MICROARRAY DETECTOR AND SYNTHESIZER

(75) Inventor: Perry Sandstrom, Madison, WI (US)

(73) Assignee: Able Signal Company, LLC, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/492,736

(22) Filed: Jul. 25, 2006

(65) Prior Publication Data

US 2006/0256332 A1 Nov. 16, 2006

Related U.S. Application Data

(63) Continuation of application No. 10/968,556, filed on Oct. 19, 2004, now Pat. No. 7,081,954, which is a continuation of application No. 10/408,870, filed on Apr. 8, 2003, now Pat. No. 6,806,954, which is a continuation of application No. 09/679,858, filed on Oct. 5, 2000, now Pat. No. 6,545,758, which is a continuation-in-part of application No. 09/640,617, filed on Aug. 17, 2000, now Pat. No. 6,567,163.

(51) Int. Cl.
*G01N 21/64* (2006.01)
(52) U.S. Cl. .................. 356/72; 356/317; 250/458.1
(58) Field of Classification Search .............. 356/72, 356/317, 458.1
See application file for complete search history.

(56) References Cited

U.S. PATENT DOCUMENTS

| | | | |
|---|---|---|---|
| 4,011,011 A | 3/1977 | Hemstreet et al. | 355/18 |
| 4,288,148 A | 9/1981 | Offner et al. | 350/453 |
| 4,683,195 A | 7/1987 | Mullis et al. | 435/6 |
| 4,683,202 A | 7/1987 | Mullis | 435/91 |
| 4,965,188 A | 10/1990 | Mullis et al. | 435/6 |
| 5,096,279 A | 3/1992 | Hornbeck et al. | 359/230 |
| 5,190,632 A | 3/1993 | Fujimiya et al. | 204/299 |
| 5,371,543 A * | 12/1994 | Anderson | 348/270 |
| 5,424,841 A | 6/1995 | Van Gelder et al. | 356/417 |
| 5,459,325 A | 10/1995 | Hueton et al. | 250/458.1 |
| 5,535,047 A | 7/1996 | Hornbeck | 359/295 |
| 5,583,688 A | 12/1996 | Hornbeck | 359/291 |
| 5,600,383 A | 2/1997 | Hornbeck | 348/771 |
| 5,631,734 A | 5/1997 | Stern et al. | 356/317 |

(Continued)

FOREIGN PATENT DOCUMENTS

DE 19940751 3/2000

(Continued)

OTHER PUBLICATIONS

Anderson and Young, Quantitative Fiber Hybridization, in Nucleic Acid Hybridization [1985].

(Continued)

*Primary Examiner*—F. L Evans
(74) *Attorney, Agent, or Firm*—Casimir Jones, S.C.

(57) ABSTRACT

The present invention relates to novel systems, devices, and methods comprising spatial light modulators for use in the reading and synthesis of microarrays. For example, the present invention provides micromirror systems for synthesizing and acquiring data from nucleic acid microarrays and systems for collecting, processing, and analyzing data obtained from a microarray.

12 Claims, 9 Drawing Sheets

U.S. PATENT DOCUMENTS

| | | | |
|---|---|---|---|
| 5,653,939 A | 8/1997 | Hollis et al. | 422/50 |
| 5,669,687 A | 9/1997 | Yang | 353/98 |
| 5,696,616 A | 12/1997 | Wagensonner | 359/201 |
| 5,744,305 A | 4/1998 | Fodor et al. | 435/6 |
| 5,753,788 A | 5/1998 | Fodor et al. | 536/22.1 |
| 5,780,857 A | 7/1998 | Harju et al. | 250/458.1 |
| 5,872,623 A | 2/1999 | Stabile et al. | 356/73 |
| 5,912,181 A | 6/1999 | Petcavich | 436/151 |
| 5,923,466 A | 7/1999 | Krause et al. | 359/389 |
| 5,981,956 A | 11/1999 | Stern | 250/458.1 |
| 6,025,601 A | 2/2000 | Trulson et al. | 250/461.2 |
| 6,038,067 A | 3/2000 | George | 359/368 |
| 6,046,808 A * | 4/2000 | Fateley | 356/330 |
| 6,542,241 B1 * | 4/2003 | Thorwirth et al. | 356/436 |
| 6,545,758 B1 * | 4/2003 | Sandstrom | 356/317 |
| 7,081,954 B2 * | 7/2006 | Sandstrom | 356/317 |

FOREIGN PATENT DOCUMENTS

| | | |
|---|---|---|
| DE | 19940752 | 4/2000 |
| DE | 19913279 | 9/2000 |
| DE | 19922942 | 11/2000 |
| WO | WO/9942813 | 8/1999 |

OTHER PUBLICATIONS

Kacian et al., Proc. Natl. Acad. Sci. USA, 69:3038 [1972]).
Chamberlin et al., Nature, 228:227 [1970].
Wu and Wallace, Genomics, 4:560 [1989].
Emmert-Buck, et al. Science 274:998 [1996].
Schafer, Applied Optics 17(7);1072 [1978].
Ih and Yen, Applied Optics 19(24):4196 [1980].
Murty, Optical Engineering 24(2):326 [1985].
McGall, et al., Proc. Natl. Acad. Sci. USA 93:13555 [1996].
McGall, et al., J. Amer. Chem. Soc. 119(22):5081 [1997].
Gasson et al., Nature Biotechnology 17:974 (1999).
Larry J. Hornbeck, "Digital Light Processing High-Brightness, High-Resolution applications," World wide Web site://www.ti.com/dlp.
Mignardi, TI Technical Journal 56-63 (1998).
Offner, Optical Engineering 14:130-132 (1975).

* cited by examiner

MICROARRAY DETECTOR AND SYNTHESIZER

The present invention is a continuation of U.S. application Ser. No. 10/968,556, filed Oct. 19, 2004, now U.S. Pat. No. 7,081,954, which is a continuation of U.S. application Ser. No. 10/408,870, filed Apr. 8, 2003, now U.S. Pat. No. 6,806,954, which is a continuation of U.S. application Ser. No. 09/679,858, filed Oct. 5, 2000, now U.S. Pat. No. 6,545,758, issued on Apr. 8, 2003, which is a continuation-in-part of application Ser. No. 09/640,617, filed Aug. 17, 2000, now U.S. Pat. No. 6,567,163, the specifications of which are herein incorporated by reference in its entireties.

FIELD OF THE INVENTION

The present invention relates to novel systems, devices, and methods comprising spatial light modulators for use in the reading and synthesis of microarrays. For example, the present invention provides micromirror systems for synthesizing and acquiring data from nucleic acid microarrays and systems for collecting, processing, and analyzing data obtained from a microarray.

BACKGROUND OF THE INVENTION

Biology and medicine have entered the age of the genomics. The completion, and imminent completion, of genomes of many important organisms (e.g., humans, mice, *C. elegans, Arabidopsis*, various crop plants, and other animals) promises to usher in advances in basic biological research and medical technology. In order to realize the enormous potential benefits to science offered by the raw data collected from genome sequencing efforts, researchers must now turn to conducting studies in functional genomics and proteomics.

The recently completed human genome project, for example, has identified the sequence of the roughly 3 billion base pairs that spell out the human genome in a four letter alphabet (i.e., 3 gigabytes of paired A:T and G:C information). The practical application of this sequence information include more detailed studies to determine where, when, and how particular genes are expressed in an organism, the sequence and functions of proteins encoded by these genes, and how proteins interact with one another and the gene sequences themselves (e.g., DNA binding proteins such as transcription factors, histones, and the like). These efforts will undoubtedly produce voluminous amounts of valuable data in which the developing techniques in the emerging discipline of bioinformatics (data mining) will seek to organize and exploit. Indeed, the amount of data generated related to genomics research is ever accelerating as high throughput methods are refined in areas like gene expression assays, protein interaction assays, in vitro or cell-based assays used in drug development and a host of clinically related genetic tests.

Hybridization microarray technology has evolved to become an important tool in large scale genomics studies. Briefly, microarrays derive their name from the small (e.g., about 20-750 micron) size of the analysis sites typically arranged in a two-dimensional matrix of probe elements on the surface of a supporting substrate. The range of microarray samples is varied. In the majority of current applications, each probe element comprises numerous identical oligonucleotide (DNA) "probe" molecules. These probes are fixed to the substrate surface and may hybridize with complementary oligonucleotide "targets" from a sample. Typically, a label (e.g., fluorescent molecule) is either attached to the target prior to the hybridization step, or to the probe/target complex subsequent to hybridization. The microarrays are then observed for the presence of detectable labels (fluorescence imaging). The presence of a label in the area encompassing a particular probe element indicates that a sequence complementary to the characteristic sequence of that element was in the analyte.

Current microarray production techniques continue to evolve to permit larger arrays and the increasingly tight packaging of probe elements such that a single substrate array might allow the detection and quantation of 100,000 or more target sequences at once. A number of microarray data acquisition technologies and methodologies are known in the art, the purpose of each of which is to acquire a collection of data reflecting the pattern of hybridization on the microarray substrate. In order to achieve meaningful data, and discriminate individual array elements, current fluorescent imaging devices (e.g., confocal scanners) must be able to represent each microarray element with multiple pixels. Obviously, the analysis of such microarrays with current scanning devices generates large volumes of data. As an example, an array of 100,000 hybridization probes in the form of 25 µm squares would be represented by an image file of over 14 Megabytes if scanned with a confocal fluorescence scanner with a 2 mm pixel size. Manipulation of image data of this size represents a significant data processing overhead. A common output format from fluorescence imaging is 16-bit graphic (.tif) files. The 16-bit format provides a sensitivity range of from 0 to 65,536 incremental signal intensity steps per image pixel per microarray fluorescence wavelength detected. The image files obtained by current scanner technology must be further processed to correlate the data to particular sites on the array. Often, these algorithms require manual intervention to set discrimination parameters or to identify data features that correspond to probe locations. Such methods are further complicated when a high-density microarray must be scanned piecemeal, with individual portions of the image subsequently fitted together. For large-scale analysis, such methods require substantial computer memory storage. Furthermore, current microarray scanners are large, cumbersome, and expensive, making large-scale analysis time consuming, complex, and inefficient.

What is needed are systems and devices to more efficiently analyze microarrays. Preferably; such systems and devices minimize data storage requirements and minimize the costs and labor of working with microarrays.

SUMMARY OF THE INVENTION

The present invention relates to novel systems, devices, and methods comprising spatial light modulators for use in the reading and synthesis of microarrays. For example, the present invention provides micromirror systems for synthesizing and acquiring data from nucleic acid microarrays and systems for collecting, processing, and analyzing data obtained from a microarray.

The present invention provides a system for detecting the presence of a sample on a microarray comprising: a spatial light modulator with controllable elements configured to correspond optically with analytical sites on a microarray, a light source capable of providing light energy for interaction with the chemical constituents on the array, and a detector capable of detecting an optical signal obtained from the microarray. The invention is not limited by the nature of the sample. Samples include, but are not limited to, molecules (e.g., nucleic acids such as DNA and RNA, PNA, lipids, polypeptides, drugs, small molecules), molecular complexes (e.g., nucleic acid hybrids, protein complexes, cell components), and reactive complexes (e.g., complexes undergoing chemical or enzymatic reactions).

The present invention is also not limited by the nature of the optical signal detectable by the detector. In some embodiments, the optical signal comprises fluorescence (e.g., generated following the excitation of a molecule comprising a fluorogenic reagent, generated by removal of a quenching group in a fluorescence resonance energy transfer, etc). In other embodiments, the optical signal comprises luminescence (e.g., bioluminescence).

While the present invention is not limited by the nature of the detector, in preferred embodiments, the detector comprises one or more non-imaging, single channel detectors (i.e., a detector configured to receive a light beam at a specific wavelength). In other preferred embodiments, the detector comprises a single non-imaging detector (i.e., a detector that is not configured to and/or not capable of receiving a video image) with a selectable optical wavelength filter.

In some preferred embodiments of the present invention, the system further comprises a light source. In some of these embodiments, the light source comprises a source of energy for light-directed synthesis of molecules. For example, in the light directed synthesis of microarray elements, a light source that provides ultra-violet light is contemplated. In particularly preferred embodiments, the light source comprises a filtered polychromatic light source with selectable output wavelengths. In further particularly preferred embodiments, the light source comprises an arc lamp (e.g., a mercury arc lamp), a metal halide lamp, or a xenon flash lamp. Moreover, a variety of other light sources (such as LEDs and lasers) find use with the present invention, some of which are described in more detail below. In some preferred embodiments of the present invention, the light source comprises a fluorescent excitation device. However, the present invention is not limited by the nature of the light source, so long as the light source is capable of generating light receivable by the spatial light modulator, wherein the light is ultimately capable of interacting with a microarray such that, if the sample to be detected is present on the microarray or in a sample exposed to the microarray, an optical signal is generated and detectable by the detector.

In some preferred embodiments of the present invention, the spatial light modulator comprises a micromirror device. In some embodiments, the micromirror device comprises at least 1000 individual micromirrors. In some preferred embodiments, the micromirror device comprises digitally-controlled micromirrors. In some preferred embodiments, the spatial light modulator comprises a Liquid Crystal Device.

In yet other preferred embodiments, the system further comprises a light projection apparatus capable of receiving light patterns produced by the spatial light modulator and capable of imaging them to a patterned microarray (e.g., to a predetermined location on the microarray based on the relative alignments of the microarray and the spatial light modulator). In particularly preferred embodiments, where the spatial light modulator comprises a micromirror array, the light from an integral number of micromirror array elements is projected to a corresponding site on the microarray. In some embodiments, the light projection apparatus comprises a reflective projection optics apparatus (e.g., an Offner Relay).

In still further embodiments of the present invention, the system may further comprise systems for holding and manipulating (e.g., physical registration) a microarray. For example, in some embodiments, the system comprises a microarray holder capable of holding a microarray. In some embodiments, the system further comprising a flow cell capable of introducing materials (e.g., a sample to be detected or to be reacted with the microarray, chemicals for use in synthesizing the microarray, wash fluid, buffers, etc.) to a microarray associated with the microarray holder.

In some embodiments of the present invention, the system further comprises a microarray in contact with the microarray holder. The microarray may be synthesized using the system of the present invention. However, in other embodiments, a microarray is obtained and placed in contact with the microarray holder. In preferred embodiments, the microarray is positioned on the microarray holder such that individual reactive sites (elements) on the array (e.g., individual probe sites in a nucleic acid microarray) correspond optically with integral numbers of spatial light modulator elements. For example, each reactive site may be positioned to correspond to an individual mirror in a micromirror array such that light reflected from the individual micromirror is capable of selectively illuminating (e.g., exciting) the reactive site on the microarray.

In other embodiments of the present invention, the system further comprises a beam splitter positioned between the light source and the spatial light modulator. In some embodiments, the beamsplitter is coated with anti-reflective coatings and/or wavelength selective coatings. In preferred embodiments, the beam splitter is capable of receiving light reacted with a microarray (e.g., optical signal from a microarray) and delivering at least a portion of the received light to the detector. In other preferred embodiments, the beam splitter is capable of receiving light from the spatial light modulator and delivering at least a portion of the received light to the detector.

In other preferred embodiments of the present invention, the system further comprises one or more filters. For example, in some embodiments, the system comprises a filter positioned at the output of the light source (e.g., to restrict the wavelengths of light that interact with the microarray). In other embodiments, the system comprises a filter positioned between the detector and the microarray. In some preferred embodiments, the filter selects a single wavelength of light. The characteristics required of the filters (e.g. passband wavelength) will vary depending on experimental protocols.

In some preferred embodiments of the present invention, the system further comprises one or more computer components (e.g., processors and/or computer memories). For example, the system may be automated through the use of a controlling computer. Such a controlling computer may control the light source to determine when light is emitted (e.g., frequency and duration of emissions), the type of light emitted, the intensity of light, and the like. The controlling computer may also determine the position of any of the above described components of the system. For example, the computer may determine the position (e.g., angle) of individual micromirrors in a micromirror assembly (e.g., determine if each individual micromirror is in an "on" or "off" position).

The system may also comprise computer components for receiving, processing, storing, transmitting, and displaying information received from the detector. For example, a computer processor may be used to receive and interpret information received from the detector. Such information may be manipulated in any number of ways. For example, processed data may comprise data obtained from a first location of the microarray mathematically transformed with data obtained from a second location of the microarray. Such processing finds use, for example, to compare results from two or more known locations on the microarray such as two different experimental sites or an experimental site and one or more control sites. Such information may include complex comparisons of multiple reactions sites on the microarray. The processed information may be provided as a single quantitative "result" which minimizes the amount of informative data that needs to be stored and analyzed. Similarly, in still other preferred embodiments, the spatial light modulator and the computer components are associated such that the system is capable of accessing any probe site in the array. Enhanced signal to noise ratios are contemplated in this method of operation. Moreover, this method of operation allows a number of comparisons between probe sites or sets of probe sites to be quickly drawn. For example, this embodiment allows for analysis, including but not limited to: a) simple fluorescence read of a particular probe site (no comparing); b) comparisons of a probe site and a reference (i.e., a blank or non-hybridizable site [eliminates background fluorescence and residual excitation light]); c) comparison of a probe site and a purposefully mismatched site (i.e., eliminates background fluorescence, residual excitation light and signal from nonspecific hybridization); d) comparison of a group of identical probe sites with an equal number of reference sites (i.e., enhances the signal to noise ratio, allows for averages of hybridization across many probes sites); e) comparison of a group of identical probe sites with an equal number of identically mismatched sites; f) comparison of a group of identical probe sites with an equal number of differently mismatched sites; g) comparison of a set of characteristic probe sites with an equal number of reference probe sites; h) comparison of a set of characteristic probe sites with an equal number of probe sites with different characteristics (i.e., useful in clinical diagnostics or expression studies); and i) combinations of the above mentioned comparisons, and other comparisons described herein. In some embodiments of the present invention, the system further comprises a computer memory capable of storing processed data received from the processor.

The present invention is not limited by the spatial configuration of the computer components. For example, the components may all be provided in one enclosed device or may be located distally from each. In some embodiments, one or more of the components is not in proximity to the other components. For example, the controlling computer, computer memory, and/or processor may be provided by a computer system located in one geographic location while the detector system may be provided in a second geographic location. In such embodiments, data may be transferred between portions of the system through any suitable means (e.g., public or private communication networks such as Internets or Intranets, phone lines, radio waves, fiber-optics systems, cable systems, satellite systems, and the like). Thus, in some embodiments, a user need not be in possession of one or more of the computer components. Such components may be "hosted" at a separated location by a service provider. For example, in some embodiments of the present invention a hospital clinical lab possesses a system comprising the detector and/or synthesizer of the present invention while the control of the equipment and/or data processing is carried out by a separate entity. In such embodiments, a hospital employee may only need to provide a sample and/or information to the device while a skilled genomics technician carries out the analysis and/or control of the process from a separate location and provides the hospital employee with meaningful, medically relevant information.

As described above, the present invention provides systems for comparing data from two or more locations on a microarray such that the information can be efficiently processed, stored, and/or interpreted. With respect to such embodiments, the present invention provides a system of comparing optical signals from two or more locations on a patterned microarray comprising: a spatial light modulator capable of receiving light from a light source and capable of directing at least a portion of said light to one or more locations on a patterned microarray and a detector capable of detecting an optical signal obtained from a patterned microarray. The system may further comprise any of the additional components described herein. In preferred embodiments, the detector is capable of receiving optical signals obtained from one or more locations on the patterned microarray. The present invention is not limited in the manner by which the optical signal is received. For example, in some embodiments, there is sequential receipt of optical signal from each of the two or more locations (e.g., wherein the system further comprises a processor capable of generating processed data, where the processed data comprises data obtained from a first location of said microarray mathematically transformed with data obtained from a second location of said microarray). In other embodiments, there is simultaneous receipt of optical signal from each of the two or more locations (e.g., optical signal from two or more sites is detected together—i.e., additively).

The present invention also provides readers comprising an excitation source, a mask, and a detector. For example, in some embodiments of the present invention, excitation light is provided to a microarray wherein a mask (e.g., a spatial light modulator) restricts either 1) the light allowed to excite specific elements on the microarray; or 2) the light allowed to pass from the microarray to a detector.

The present invention further provides methods for using the systems and devices of the present invention. In some embodiments, any of the above systems are used for synthesizing microarrays. In other embodiments, the systems are used for detecting signal generated from microarrays. For example, the present invention provides a method for detecting optical signal generated from a microarray comprising: providing a patterned microarray comprising a plurality of reaction sites, a light source, a spatial light modulator, and a detector; exposing the spatial light modulator to light from the light source under conditions such that one or more of the plurality of reaction sites on the patterned microarray are excited to produce optical signal; and detecting the optical signal with the detector. Such methods find a wide variety of uses including, but not limited to, detection of target molecules in a sample, characterization of molecules, and screening for molecules with desired properties (e.g., drug screening).

In some embodiments of the present invention, the systems and devices employ excitation and/or excitation masks. For example, certain preferred embodiments of these systems and devices employ spatial light modulators capable of selectively creating excitation or emission masks capable of passing or absorbing light (e.g., micromirror arrays, LCDs, FLCDs, and the like).

In still other preferred embodiments, the systems and devices of the present invention comprise data acquisition systems. The present invention contemplates that in some such embodiments, the data acquisition systems further comprise a plurality of analog and/or digital components. As noted above, the present invention contemplates data acquisition systems capable of receiving input from photodetectors, manipulating this input, and generating a useful output signal corresponding to a characterization of one or more sites on a microarray. The present invention is not limited by the manner the data acquisition system outputs data, indeed, output from the system may be further manipulated, recorded, or displayed by a processor, a memory device, a monitor (e.g., video monitor), a graph generating device, and the like.

In some preferred embodiments of the present invention, the systems and devices are used for patterning non-biological molecules. For example, the present invention has applications in the fields of electronics, materials engineering, the development of nanoscale devices, and the like.

DEFINITIONS

Figure 1:
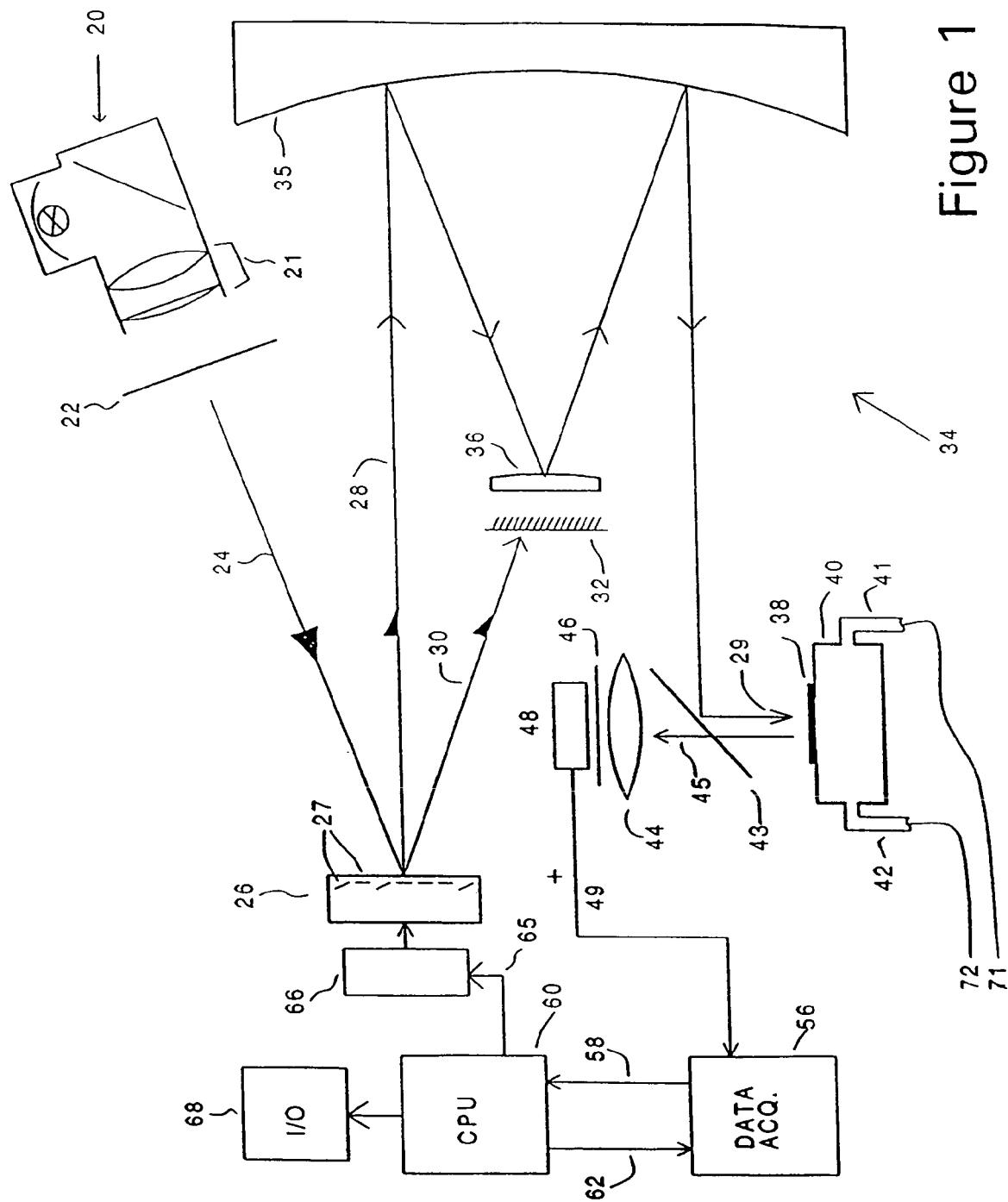
FIG. 1 shows a system using a micromirror spatial light modulator.

To facilitate an understanding of the present invention, a number of terms and phrases are defined below:

As used herein "light beam" refers to directed light, for example, comprised of either a continuous cross-section or a plurality of convergent or divergent sub-beams (e.g., a patterned beam). This term is meant to include, but is not limited to, light emitted from a light source, light reflected upon striking a reflecting device (e.g., a micromirror), and the like.

As used herein, the term "collimated light" refers to a beam of light having substantially parallel rays. The term is meant to include quasi-collimated light.

As used herein, "optical signal" refers to any energy (e.g. photodetectable energy) from a sample (e.g., produced from a microarray that has one or more optically excited [i.e., by electromagnetic radiation] molecules bound to its surface).

As used herein, "filter" refers to a device or coating that preferentially allows light of a characteristic spectra to pass through it (e.g., the selective transmission of light beams).

As used herein, the term "spatial light modulator" refers to devices that are capable of producing controllable (e.g., programmable by a processor, or pre-directed by a user), spatial patterns of light from a light source. Spatial light modulators include, but are not limited to, Digital Micromirror Devices (DMDs) or Liquid Crystal Devices (LCDs). LCD may be reflective or transmissive of the directed (e.g., spatially modulated) light.

"Polychromatic" or "broadband" as used herein, refers to a plurality of electromagnetic wavelengths emitted from a light source.

As used herein, "microarray" refers to a substrate with a plurality of molecules (e.g., nucleotides) bound to its surface. Microarrays, for example, are described generally in Schena, "Microarray Biochip Technology," Eaton Publishing, Natick, Mass., 2000. Additionally, the term "patterned microarrays" refers to microarray substrates with a plurality of molecules non-randomly bound to its surface.

As used herein, the term "micromirror array" refers to a plurality of individual light reflecting surfaces that are addressable (e.g., electronically addressable in any combination), such that one or more individual micromirrors can be selectively tilted.

As used herein, the term "optical detector" or "photodetector" refers to a device that generates an output signal when irradiated with optical energy. Thus, in its broadest sense the term optical detector system is taken to mean a device for converting energy from one form to another for the purpose of measurement of a physical quantity or for information transfer. Optical detectors include but are not limited to photomultipliers and photodiodes.

As used herein, the term "photomultiplier" or "photomultiplier tube" refers to optical detection components that convert incident photons into electrons via the photoelectric effect and secondary electron emission. The term photomultiplier tube is meant to include devices that contain separate dynodes for current multiplication as well as those devices which contain one or more channel electron multipliers.

As used herein, the term "photodiode" refers to solid-state light detector types including, but not limited to PN, PIN, APD and CCD.

As used herein, the term "TTL" stands for Transistor-Transistor Logic, a family of digital logic chips that comprise gates, flip/flops, counters etc. The family uses 0Volt and 5Volt signals to represent logical "0" and "1" respectively.

As used herein, the term "dynamic range" refers to the range of input energy over which a detector and data acquisition system is useful. This range encompasses the lowest level signal that is distinguishable from noise to the highest level that can be detected without distortion or saturation.

As used herein, the term "noise" in its broadest sense refers to any undesired disturbances (i.e., signal not directly resulting from the intended detected event) within the frequency band of interest. Noise is the summation of unwanted or disturbing energy introduced into a system from man-made and natural sources. Noise may distort a signal such that the information carried by the signal becomes degraded or less reliable.

As used herein, the term "signal-to-noise ratio" refers the ability to resolve true signal from the noise of a system. Signal-to-noise ratio is computed by taking the ratio of levels of the desired signal to the level of noise present with the signal. In the present invention, phenomena affecting signal-to-noise ratio include, but are not limited to, detector noise, system noise, and background artifacts. As used herein, the term "detector noise" refers to undesired disturbances (i.e., signal not directly resulting from the intended detected energy) that originate within the detector. Detector noise includes dark current noise and shot noise. Dark current noise in an optical detector system results from the various thermal emissions from the photodetector. Shot noise in an optical system is the product of the fundamental particle nature (i.e., Poisson-distributed energy fluctuations) of incident photons as they pass through the photodetector.

As used herein, the term "system noise" refers to undesired disturbances that originate within the system. System noise may include noise contributions from signal amplifiers, electromagnetic noise that is inadvertently coupled into the signal path, and fluctuations in the power applied to certain components (e.g., a light source)

As used herein, the term "background artifacts" include signal components caused by undesired optical emissions from the microarray. These artifacts arise from a number of sources, including: non-specific hybridization, intrinsic fluorescence of the substrate or reagents, incompletely attenuated fluorescent excitation light, and stray ambient light. The noise of an optical detector system can be determined by measuring the noise of the background region and noise of the signal from the microarray feature.

As used herein, the term "processor" refers to a device that performs a set of steps according to a program (e.g., a digital computer). Processors, for example, include Central Processing Units ("CPUs"), electronic devices, or systems for receiving, transmitting, storing and/or manipulating digital data under programmed control.

As used herein, the term "memory device," or "computer memory" refers to any data storage device that is readable by a computer, including, but not limited to, random access memory, hard disks, magnetic (floppy) disks, compact discs, DVDs, magnetic tape, and the like.

The term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified", "mutant", and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in either a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification and hybridization reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q-replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified, away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to a molecule (e.g., an oligonucleotide, whether occurring naturally as in a purified restriction digest or produced synthetically, recombinantly or by PCR amplification), that is capable of hybridizing to another molecule of interest (e.g., another oligonucleotide). When probes are oligonucleotides they may be single-stranded or double-stranded. Probes are useful in the detection, identification and isolation of particular targets (e.g., gene sequences). In some embodiments, it is contemplated that probes used in the present invention are labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular label. With respect to microarrays, the term probe is used to refer to any hybrididizable material that is affixed to the microarray for the purpose of detecting "target" sequences in the analyte.

As used herein "probe element" or "probe site" refers to a plurality of probe molecules (e.g., identical probe molecules) affixed to a microarray substrate. Probe elements containing different characteristic molecules are typically arranged in a two-dimensional array, for example, by microfluidic spotting techniques or by patterned photolithographic synthesis.

As used herein, the term "target," when used in reference to hybridization assays, refers to the molecules (e.g., nucleic acid) to be detected. Thus, the "target" is sought to be sorted out from other molecules (e.g., nucleic acid sequences) or is to be identified as being present in a sample through its specific interaction (e.g., hybridization) with another agent (e.g., a probe oligonucleotide). A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified." In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications. With PCR, it is possible to amplify a single copy of a specific target sequence in genomic DNA to a level detectable by the device and systems of the present invention.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature in contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "coding region" when used in reference to a structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets which specify stop codons (i.e., TA, TAG, TGA).

As used herein, the term "purified" or "to purify" refers to the removal of contaminants from a sample.

The term "recombinant DNA molecule" as used herein refers to a DNA molecule that is comprised of segments of DNA joined together by means of molecular biological techniques.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (e.g., 4, 5, 6, . . . , 100, . . .).

The term "recombinant protein" or "recombinant polypeptide" as used herein refers to a protein molecule that is expressed from a recombinant DNA molecule.

As used herein the term "biologically active polypeptide" refers to any polypeptide which maintains a desired biological activity.

As used herein the term "portion" when in reference to a protein (as in "a portion of a given protein") refers to fragments of that protein. The fragments may range in size from four amino acid residues to the entire amino acid sequence minus one amino acid (e.g., 4, 5, 6, . . . , 100, . . . ).

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "test compound" refers to any chemical entity, pharmaceutical, drug, and the like that can be or might be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention.

As used herein, the term "sample" is used in its broadest sense. In one sense it can refer to a tissue sample. In another sense, it is meant to include a specimen or culture obtained from any source, as well as biological. Biological samples may be obtained from animals (including humans) and encompass fluids, solids, tissues, and gases. Biological samples include, but are not limited to blood products, such as plasma, serum and the like. These examples are not to be construed as limiting the sample types applicable to the present invention.

GENERAL DESCRIPTION OF THE INVENTION

The present invention relates to novel systems, devices, and methods comprising spatial light modulators for use in the reading and synthesis of microarrays. For example, the present invention provides micromirror systems for synthesizing and reading nucleic acid microarrays and systems for collecting, processing, and analyzing data obtained from a microarray.

For example, the present invention provides microarray readers capable of being configured with a wide variety of microarray formats. In preferred embodiments, the reader comprises a spatial light modulator that allows specific elements (e.g., specific probe sites in a nucleic acid microarray) on a microarray to be detected or combinations of sites to be detected simultaneously or in series (e.g., to compare detectable signals at two or more separate locations on the microarray). In preferred embodiments, the reader comprises a single-channel non-imaging detection element that receives detectable data (e.g., the presence or absence of emitted fluorescence or luminescence) from the microarray. In such embodiments, the data to be processed and stored using the device is greatly simplified compared to currently available systems (e.g., fluorescent imaging) as single data points can represent each array site or combination of sites to be detected (e.g., as opposed to scanning techniques that scan the entire surface of an array with multiple pixels per array element).

Certain preferred embodiments of the present invention also provide a system for synthesizing microarrays. For example, the spatial light modulator can be used in conjunction with a light source to direct light to specific locations on the surface of a solid substrate to generate a patterned array. A microarray generated using this system may be directly used in an assay (e.g., a hybridization assay) with the system further providing detection capabilities. In such embodiments, the location of each element to be read on the microarray exists at a known location relative to the reader.

One embodiment of the present invention comprises a light source, a spatial light modulator, and a microarray. Another embodiment of the present invention comprises a light source, a spatial light modulator, a microarray, and a photodetector. In some embodiments, the invention further comprise one or more filters and lenses that discriminate preferred light wavelengths, condense light beams, collimate light beams, and generally remove interference and noise. Rotating filter carriers, and other arrangements, that allow the manual or automated selection of a particular filter from a number of available filters are also specifically contemplated. Additionally, the lenses, filters and mirrors of the present invention may further comprise coatings to reduce interference, noise, and undesired reflections in the system. Even more particularly, the invention may further comprise an optical projection system that directs the light from a light source after undergoing spatial modulation by the spatial light modulator onto an array surface. In some embodiments, the optical relay system is an Offner Relay that translates light to the array when the microarray and the spatial light modulator have the same form factor (assuming 1:1 projection optics). Yet even more particularly, the present invention comprises digital and analog signal processing elements that preferably distinguish the desired signal from various noise sources, thereby facilitating the discrimination of signals from distinct microarray elements. As described herein, these components and methods also allow direct comparisons of signal between individual microarray elements or groups of elements. In these embodiments, microarray elements may comprise target or probe elements or control elements. Similarly, the present invention comprises digital and analog controls preferably allowing the alignment of microarrays not fabricated by the system and device, and also to control the actuation of the spatial light modulator employed.

In still other embodiments the spatial light modulator (e.g., a micromirror array) is capable of random-accessing a discrete site on the microarray surface such that differential measurements of array features can be made. In some of these embodiments, the spatial light modulator is used to selectively transmit light between discrete features of the microarray and the detector (i.e., an emission mask). In other embodiments, the spatial light modulator is used to selectively transmit fluorescent excitation light to discrete features on the microarray (i.e., an excitation mask). In still other embodiments, the spatial light modulator is arranged to serve either function. In certain embodiments, the detectors employed in the present invention comprise photomultiplier tubes. In certain other embodiments, the detectors employed comprise photodiodes.

In certain embodiments, the present invention comprises a read-only device comprising an excitation light source, a spatial light modulator, and a single channel non-imaging detector. In certain of these embodiments, the present invention further comprises a LCD spatial light modulator positioned preferentially in the light path from microarray to detector (used as an emission mask), or light source and microarray (used as an excitation mask). In still other embodiments, where an LCD is used as an excitation mask, it is contemplated that the light source and spatial light modulator may function as a microarray synthesizer employing short wavelength light. The present invention further contemplates that optical access to the microarray may be made through one or more transparent parts of the flow cell.

In some embodiments of the present invention, the reader/synthesizer comprises a selectively filtered polychromatic light source, a spatial light modulator, a detector, and a mounting device for holding a microarray device. In some preferred embodiments where the system provides synthesis capabilities, filtered light from the polychromatic light source is directed to the spatial light modulator (e.g., micromirror) which directs at least a portion of the light to one or more locations on a solid substrate upon which an array is to be fabricated. The light provides the energy necessary for chemically synthesizing the array. In some embodiments, the light source filter used for synthesis is of a passband wavelength necessary for light-directed synthesis of the array (See e.g., U.S. Pat. No. 5,753,788, incorporated herein by reference in its entirety). The ingredients of the array elements (e.g., nucleotides for the generation of nucleic acid arrays) may be provided to the substrate through a flow cell. By rationally directing light to particular locations on the substrate, in a manner that is synchronous with the introduction of different array fabrication chemicals, a desired array is generated. In a preferred detection method of the present invention, the light source filter is of a passband wavelength suitable for exciting an optical signal from a target site if the appropriate assay conditions are met (e.g., if a fluorescently-labeled nucleic acid hybridization event has occurred at the site). Target sites on the array are exposed to light from the spatial light modulator, allowing for selective excitation of one or more target sites at a time. The detector monitors the optical signal from the microarray. The detector signal is acquired and stored in a manner that is synchronous with the control of the excitation patterns produced by the spatial light modulator. In some embodiments, the different wavelengths necessary for performing synthesis and detection may be selected from the same polychromatic light source using a filter selection mechanism (e.g., a filter wheel).

The detection capabilities of the present invention find use with a variety of microarrays and assay systems. For example, the detection system finds use with nucleic acid microarrays. Reactions (e.g., hybridization reactions, protein/nucleic acid binding reactions, enzymatic reactions, and the like) that occur at specific locations (i.e., on specific elements) on the microarray can be detected in a wide variety of formats. For example, a reaction event at a single location can be detected. Likewise, reaction events at multiple locations can be detected simultaneously or in sequence. Multiple locations may be detected, for example, to analyze families of sequences together (e.g., families of short oligonucleotides that in combination represent a gene) and to compare "experimental" sites to one or more "control" sites (e.g., positive control, negative control, blank, etc.).

The detection system also finds use with peptide arrays. For example, it may be used to detect the binding of arrayed peptides to potential binding partners (e.g., other peptides, nucleic acids, lipids, receptor binding factors, hormones, drugs, co-factors, etc.). For nucleic acid, peptide, and other types of arrays, the detection system finds use in screening assays (e.g., drug screening assays). For example, a candidate compound (e.g., a drug) suspected of having biological activity in the presence of another compound can be exposed to an array comprising said compound to determine if there is an interaction. Such screening methods can, for example, determine the ability of compounds to prevent the binding of two other agents to one another (e.g., prevent the binding of two proteins to one another) by detecting the presence or absence of binding complexes in the presence of the compound.

DETAILED DESCRIPTION OF THE INVENTION

The present invention utilizes a light source, spatial light modulator, microarray, and a detector in the reading and synthesis of microarrays. For example, the present invention provides micromirror systems for synthesizing and detecting nucleic acid microarrays and systems for collecting, processing, and analyzing data obtained from a microarray. Certain preferred embodiments of the systems, devices, and methods of the present invention are described in more detail below in the following sections: I) Synthesis; II) Hybridization; III) Detection; and IV) Exemplary System Configurations. The following examples are provided in order to demonstrate and further illustrate certain preferred embodiments and aspects of the present invention and are not to be construed as limiting the scope thereof.

I. Synthesis

Microarrays provide a powerful tool for the analysis of numerous types of biomolecules, as well as other organic and inorganic samples. Analysis of nucleic acids is one main area of microarray development. Microarray techniques have been developed for comparative studies of DNA, RNA, and mRNA from a number of organisms (e.g., vertebrates, invertebrate, plants, yeasts, fungi, bacteria, and viruses). Some microarray applications use the "polymerase chain reaction" (PCR) for generating sufficient quantities of target or probe oligonucleotides. Alternatively, nucleic acid synthesis methods can be used for generating precise oligonucleotide target and probe sequences. Microarrays can also be fabricated with purified or synthetic polypeptides targets and probes. Similarly, whole cells or fragments of cells can be assayed in microarray format. For example, techniques such as laser capture microdissection (LCM) technology (Emmert-Buck, et al. Science 274:998 [1996]) when combined with T7-based RNA amplification allow for functional analysis of human cells. Further refinements of these techniques will ultimately allow for the building of 3-D databases of gene expression profiles from whole organisms. Adding a fourth dimension (e.g., a temporal component) would provide 4-D databases such that the interaction of drugs, hormones, and other stimuli could be monitored quantitatively on a cell-by-cell basis in intact cells and organisms.

In preferred embodiments, the microarray elements of the present invention are supported by association with one or more solid or semi-solid substrates. For example, test array supporting substrates may comprise planar (i.e., 2 dimensional) glass, metal, composite, or plastic slides and wafers, biocompatible or biologically unreactive compositions, and porous or structured (i.e., 3 dimensional) substrates of the same, or similar, composition as those utilized in 2 dimensional substrates. For example, common planar arrays include 1 in.×3 in. microscope slides (1×25×76 mm) and yield approximately 19 $cm^2$ of surface area (enough surface area for >100,000 array features using current microspotting and ink-jetting arraying technologies). Currently microscope slides are being manufactured using ultraflat substrates (ultraflat, also known as "optically flat,") surfaces that help to eliminate data acquisition errors resulting from out of focus array elements on uneven substrate surfaces) (TeleChem, Sunnyvale, Calif.). Specially manufactured, or chemically derivitized, low background fluorescence substrates (e.g., glass slides) are also commercially available. In yet other embodiments, planar microarray substrates further comprise cover slips, gaskets, or, other enclosures that protect the array elements and provide channels for the flow of chemical and reagents for microarray preparation, hybridization, labelling, etc. Microarray elements may be prepared and analyzed on either the top or bottom surface of the planar substrate (i.e., relative to the orientation of the substrate in the data acquisition device of the present invention).

In those embodiments that make use of 3-dimensional microarray substrates, the present invention contemplates substrates comprising spheres, waffled structures, rods, cones, tubes (e.g., capillary tubes), or other geometric forms suitable for supporting microarrays. In other embodiments of the present invention, common commercially available or chemically derivitized microwells (e.g., 96 well plastic substrates) support the microarray elements.

Other embodiments of the present invention comprise microarray reaction chambers (e.g., machined, fabricated, or otherwise formed metal or plastic surfaces) that support microarray element production (e.g., light directed maskless microarray fabrication) and data acquisition. For example, commercially available microarray cassettes and modules optimized for data acquisition by the methods and compositions of the present invention are contemplated for use with the present invention (e.g., GENECHIP probe arrays, Affymetrix, Inc., Santa Clara, Calif.; FLOW-THRU CHIP, Gene Logic, Inc., Gaithersburg, Md.). In especially preferred embodiments, the microarray substrates and light directed maskless array fabrication techniques are those described in WO/9942813 (hereby incorporated by reference in its entirety).

Those skilled in the art well appreciate that certain substrate preparation steps may be necessary in order to prepare the chosen substrate for receiving microarray element features. For example, glass or plastic substrate slides are often treated under harsh conditions with strong acids or detergents to remove undesired organic compounds and lipids prior to association with microarray probe features (e.g., nucleic acid sequences).

In some embodiments, the microarray substrates (e.g., glass slides) are associated or derivitized with one or more coatings and/or films that increase microarray element probe-to-substrate binding affinity. Increased microarray probe binding to substrates leads to increased microarray probe retention during the various stages of microarray preparation and analysis (e.g., hybridization, staining, washing, scanning stages, and the like, of microarray preparation and analysis). Additionally, any coatings or films applied to the microarray substrates should be able to withstand any subsequent treatment steps (e.g., photoexposure, boiling, baking, soaking in warm detergent-containing liquids, and the like) without substantial degradation or disassociation from the microarray substrate. Examples of substrate coatings and films include, vapor phase coatings of 3-aminopropyltrimethoxysilane, as applied to glass slide products from Molecular Dynamics, Sunnyvale, Calif. Generally, hydrophobic substrate coatings and films aid in the uniform distribution of hydrophilic probes on the microarray substrate surfaces. Importantly, in those embodiments of the present invention that employ substrate coatings or films, those coatings or films are substantially non-interfering with microarray processing steps (e.g., non-fluorescent), additionally, any coatings or films applied to the substrates either increase target binding to the microarray probes or at least do not substantially impair target binding. While an understanding of the mechanisms is not necessary for practicing the present invention and the present invention is not limited to any particular mechanism, it is believed that hydrophobic microarray substrate coatings contribute to uniform microarray probe distribution by providing increased surface tension that retards the spread of microarray probe material after its application to the substrate. Other applied substrate coatings and films approaches comprise associating chemical agents to the microarray substrate selected for their reactivity with microarray probes or targets. For example, TeleChem, Sunnyvale, Calif., provides organo-amine and organo-aldehyde reactive groups at a concentration of about $5 \times 10^{12}$ reactive groups/cm$^2$. Such reactive groups increase the binding affinity of nucleic acids, proteins, small molecules, extracts, and whole or fragmented cells, etc. to microarray substrates. Substrate coatings and films are preferentially applied as monolayers. In other embodiments, where two or more coatings or films are associated with a microarray substrate, the coatings may be applied simultaneously or sequentially, such that the layers form a substantially confluent monolayer, or such that the coatings remain separated as distinct features. In particular embodiments, amine- or lysine-coated substrates absorb/adsorb nucleic acid probe element molecules, especially when glass substrates are utilized. In other embodiments, nitrocellulose derivitized substrates are contemplated as suitable microarray substrates.

The present invention is not limited to substrates derivitized by addition or modification of organo-amine or organo-aldehyde, any derivitization that results in desired sample binding affinity, or improved microarray handling and test results are also contemplated. The utility of proposed microarray substrate coating, film, or deritivization, can be determined by 1) preparing one or more microarray substrates comprising the proposed coating, film or deritivization, that further comprise a plurality of known microarray element features; 2) preparing one or more identical microarray substrate, comprising control substrates that omit the proposed microarray substrate coating, film or derivitization; 3) performing like reaction steps (e.g., nucleic acid hybridization and staining) on the substrates; 4) acquiring data from the respective microarrays substrates; and 5) interpreting a change in the data acquired from control (i.e., nonderivitized substrates) and those substrates comprising the proposed microarray substrate coating, film, or derivization.

A variety of environmental conditions may affect microarray fabrication. For example, humidity, temperature, exposure to light or chemical, and dust. For example, low ambient humidity may cause excessive loss of probe element from freshly printed microarrays or from the print or pin heads prior to deposition. In embodiments that utilize printing or contact methodologies for depositing probe elements, measures are taken to minimize probe carry over (e.g., washing deposition devices between depositions of dissimilar chemicals). In preferred embodiments, after microarray elements are deposited on the substrates, unbound probe molecules are usually removed (e.g., washed from the substrate surface). In preferred embodiments, the characteristics of substrate coatings or films associated with microarrays substrates can be analyzed by surface analysis tools and techniques (e.g., electron spectroscopy for chemical analysis [ESCA], or spectroscopic ellipsometry). In those embodiments employing ESCA techniques for substrate surface analysis, the substrate surface is bombarded with photons in the form of X-rays. Electrons are emitted from the surface with an energy characteristic (i.e., profile) of their atomic source. The detection of surface emitted electrons bearing energy profiles similar to nitrogen can be used to quantify the presence of amine groups in microarray substrate surface coatings and films. Spectroscopic ellipsometry is an optical technique for quantifying surface characteristics. This technique measures the change in polarization of light reflected from a surface to provide a determination of surface coating thickness. This technique can resolve surface film thicknesses from ten to several thousand angstroms.

In preferred embodiments of the present invention directed to microarray synthesis, the present invention contemplates the reuse of individual microarray substrates in multiple assays. In certain of these embodiments, the microarray substrate remains fixed to the device (e.g., immobilized in a microarray holder) after being read, and the fabricated probes, synthesis and detecting chemicals and other reagents are then substantially removed (e.g., flushed away) from the substrate such that subsequent microarray probes may be fabricated on substrate. It is contemplated that the sensitivity of some probe molecules (e.g., oligonucleotides) to short wavelength light may be exploited for removing fabricated probes from the microarray substrate. For example, in preferred embodiments, a short wavelength UV (e.g., 280 nm) filter may be employed to select a "cleaning light" from the light source. In some embodiments, the "cleaning light" may be directed by a spatial light modulator to any or all probe sites while suitable wash buffers and/or detergents are contacted to the microarray substrate.

In some embodiments of the present invention, the microarray substrates comprise identifying markers. The present invention contemplates that such identification be either integral to the microarray substrate or otherwise affixed to the substrates (e.g., tags, stickers, stamps, and the like). For example, the microarray substrates may comprise imprinted, or affixed, alphanumeric, mathematical, or other symbols and characters that represent characteristics about the particular microarray, test sample, or about the source of the microarray targets. More particularly, in some preferred embodiments, the microarray substrates comprise machine readable encoding (e.g., bar codes). The present invention contemplates that microarray substrates marked with machine readable encoding convey information about one or more of the characteristics of the microarray, for example, batch number, reagents and hybridization reaction conditions, microarray feature information, microarray tracking information, diagnostic information about a particular subject or experiment, and the like. In those embodiments comprising machine readable microarray substrates, the present invention may comprise one or more devices selected to perceive the information represented in the machine readable encoding. In yet other embodiments of the present invention, the microarray substrates comprise raised or tactile identifying markers. The present invention contemplates that those embodiments of microarray substrates that comprise tactile markers comprise either raised areas or indentations that represent alphanumeric, mathematical or other symbols and characters that represent characteristics about the particular microarray, test sample, or about the source of the microarray targets.

In some embodiments of the present invention, the microarray substrate comprises one or more chamfers, grooves, pins, cleats, coupling, or ferrules, and the like, for securing the substrate during preparation and processing steps, or for immobilizing the microarray substrate during reading or synthesis of the microarray.

Numerous techniques for associating microarray elements with microarray substrates exist. For example, microarray elements may be located on suitable substrates by non-contact or contact systems. In particular, non-contact systems typically comprise ink-jet like, or piezoelectric printing technologies. Target microarray elements in solution are associated with a print head which is then moved to an appropriate coordinate above the substrate. The solution comprising the target elements is then forced onto the substrate. In preferred embodiments, the substrate is prepared or derivitized to better adhere the target elements. In certain of these embodiments, target deposition is accomplished by piezoelectric printing technologies. Piezoelectric printing equipment suitable for fabricating microarrays is available, for example, from Packard Instrument Co., Meridan, Conn., and Incyte Pharmaceuticals, Palo Alto, Calif. In certain other of these embodiments, target deposition is accomplished by syringe-solenoid printing technologies. Syringe-Solenoid printing technology suitable for fabricating microarrays is available, for example, from Cartesian Technologies, Irvine, Calif. In some embodiments, non-contact printing technologies fabricate microarrays on porous on semi-solid substrates.

Contacting microarray printing technologies utilize slender pins, with or without fluid retaining grooves and wells, that are contacted (i.e., "tapped") directly to the surface of the microarray substrate. Examples of rigid contact type printing devices include, quills, capillaries, tweezers, split pins (e.g., TeleChem International, Inc., Sunnyvale, Calif.), and PIN-and-RING (Genetic MicroSystems, Inc., Alameda, Calif.).

In some preferred embodiments of the present invention, the microarrays are fabricated using photolithographic technologies. For example, U.S. Pat. Nos. 5,744,305, 5,753,788, and 5,770,456 (herein incorporated by reference in their entireties) describe photolithographic techniques for directly fabricating microarray elements on a rigid substrate using photolabile protecting groups and a number of fixed-pattern light masks for selectively deprotecting array elements for nucleoside concatenation at each base addition step. A "maskless" microarray fabrication technology is also known (See e.g., WO/9942813). In a preferred embodiment, the present invention can be used to acquire data sets from microarrays fabricated utilizing the maskless array fabrication technology disclosed in WO/9942813. In another embodiment, microarrays are fabricated in a manner, in whole, or in part, similar to that described in WO/9942813 by the system of the present invention, and then "read" (i.e., data is acquired from the microarray) by the system of the present invention.

The present invention is not intended to be limited to acquiring data sets from any one of the particular types of arraying technologies briefly described herein. Indeed, the present invention contemplates use with any microarray substrate with probe elements suitable, or optimizable, for data acquisition by the methods and apparatuses of the present invention.

The present invention contemplates microarray elements comprising one or more biologically, or industrially important molecules. For example, target elements may comprise, but are not limited to, oligonucleotides (e.g., nucleic acids) either partially or wholly single or double stranded, or combinations additionally of DNA and RNA, proteins or fragments of proteins, polysachrides, lipids and fatty acids, steroids, polysachrides, etc. In preferred embodiments, the target elements comprise oligonucleotides. In other preferred embodiments, the target elements comprise proteins or molecules that selectively bind to proteins.

A range of microarray substrate sizes and shapes are contemplated. In some embodiments, the substrates are rigid (e.g., slides and the like). In yet other embodiments, the microarray substrates are gels or polymers. In still other embodiments, microarray substrates further comprise chambers, vessels or channels (e.g., for target or sample fabrication, labeling, or delivery).

In embodiments where nucleic acids (e.g., DNA) comprise the probe elements, a hybridization step is typically carried out to bind a target, either labeled or unlabeled, to the probe elements. More generally, the probe elements are used to determine the existence and or the extent of appearance of a particular complementary molecule in a sample contacted to the microarray and its probe elements. Typically the probe elements bound to the microarray substrate themselves interact with binding partners when contacted with a solution containing a sample. One or more labeling steps are performed to produce an optically detectable change on the surface of the microarray where hybridization has occurred.

II. Hybridization

In preferred embodiments of the present invention, methods are provided for the hybridization of microarray probes to labeled or unlabeled targets. In some cases the probes are oligonucleotides fabricated on the microarray substrate by the device and system of the present invention. The present invention is not intended to be limited by the type or kind of probe associated with the microarray substrate. In other embodiments, microarray substrates with associated probe elements are provided and optimized for use in the devices and system of the present invention. Alternative embodiments of the microarray targets and probes contemplated by the present invention are provided herein in other sections.

The particular hybridization reaction conditions can be controlled to alter hybridization (e.g., increase or decrease oligonucleotide binding stringency). For example, reaction temperature, concentrations of anions and cations, addition of detergents, and the like, can all alter the hybridization characteristics of microarray probe and target molecules.

Using the detection method described below, one or more specific array sites can be monitored while the array is being exposed to a sample. The monitored sites may be special sites with characteristics (e.g., sequences) known to hybridize with material naturally in or added to the sample. One or more groups of analytical (normal) probe sites may also be monitored together, to provide an average signal representing a relative level of hybridization across the microarray.

In some embodiments of the present invention, it is contemplated that special hybridization monitoring sites may be created by "corrupting" the synthesis at those sites during light-directed synthesis of the microarray by the present invention. These sites are created during synthesis of the microarray by limiting the amount of light provided to these sites for deprotection. This may be effected by briefly pulsing the "on" state of the spatial light modulator elements associated with these sites under programmed control. If, for example, the deprotection is manifest at only one-fourth of the molecules in these probe sites during each nucleotide addition step, a quasi-random collection of oligonucleotide sequences of varying lengths will be created in these probe sites. It is further contemplated that probe sites with these characteristics will exhibit a particularly non-specific hybridization to target material. This lack of specificity may provide hybridization monitor sites which are relatively consistent between different target-bearing samples.

Figure 8:
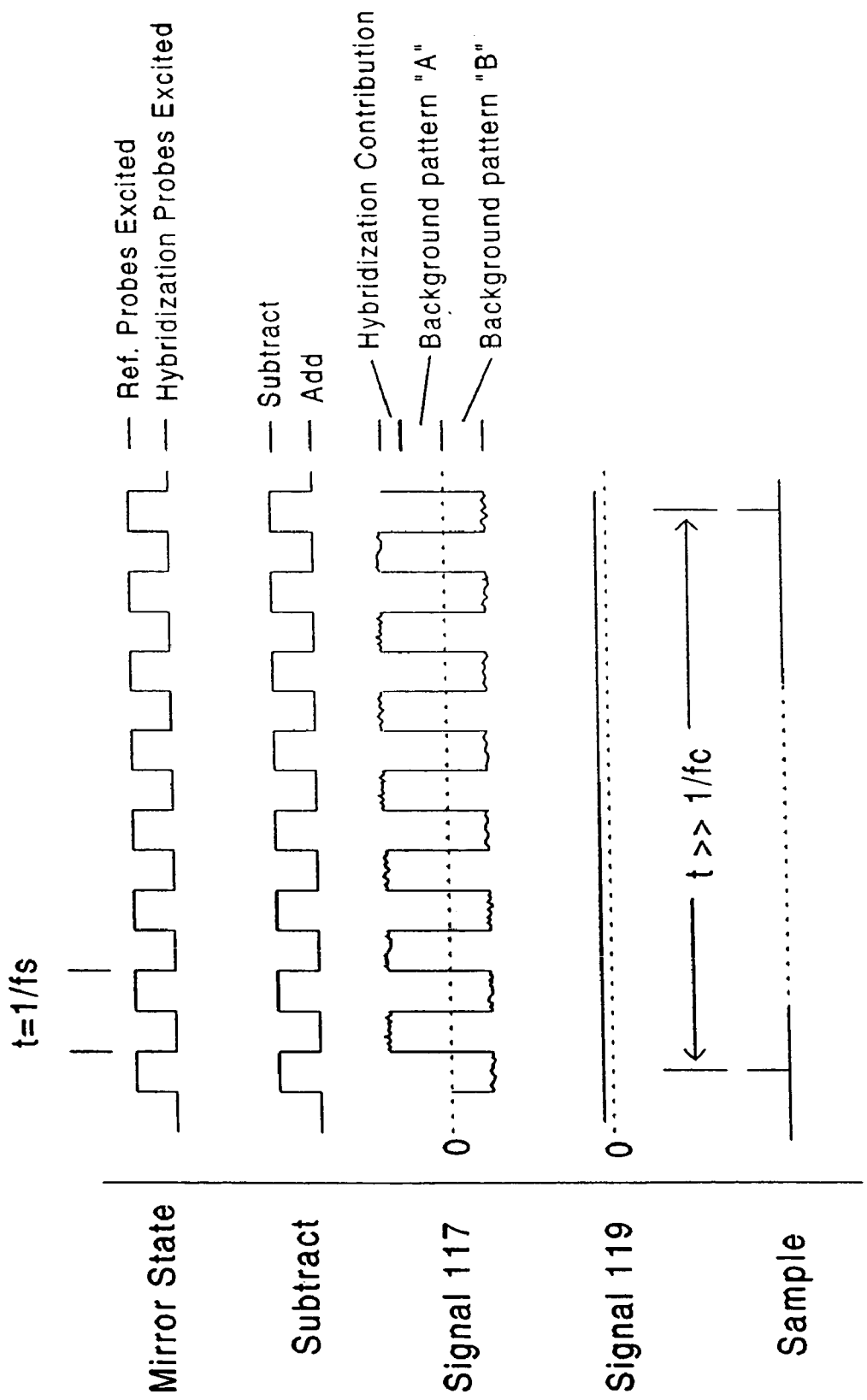
FIG. 8 illustrates the timing relationship between signals in one embodiment of FIG. 7.

Regardless of the type of hybridization monitoring sites used, the hybridization signal detected from these sites is compared to a pre-determined threshold, thereby providing an endpoint signal that can be used to indicate sufficient hybridization. The endpoint signal may be used to automatically terminate the delivery of sample-containing fluid to a flow cell. A general algorithm for controlling analyte delivery by monitoring hybridization is shown in FIG. 8.

III. Detection

To generate data from microarray assays some signal is detected that signifies the presence of, or absence of, the sequence of, or the quantity of the assayed compound or event. In preferred embodiments, the signal involves a measurement of fluorescence. Briefly, fluorescence occurs when light is absorbed from an external (excitation) source by a fluorescent molecule (a fluorophore) and subsequently emitted. The emitted light is of a lower energy (longer wavelength) than the absorbed light because some of the excitation energy is dissipated upon absorption. The characteristic spectral shift between excitation and emission wavelengths of a particular fluorophore is called the Stokes shift. Discrimination between excitation wavelengths and emission wavelengths improves the signal to noise ratio and dynamic range of the detector system by substantially removing background fluorescence and scattered excitation light from fluorophore-specific emission. The present invention contemplates a number of fluorescence techniques. For example, in some embodiments, one or more spectrums of excitation or emission light are passed through linearly polarizing filters to selectively excite fluorophores in a particular orientation. In other embodiments of the present invention, time-resolved fluorescence is utilized to obtain information on the reaction kinetics of macromolecules.

In embodiments where the microarray comprises nucleic acids, the present invention further contemplates direct and indirect labeling techniques. For example, direct labeling incorporates fluorescent dyes directly into the targets that hybridize to the microarray associated probes (e.g., dyes are incorporated into targets by enzymatic synthesis in the presence of labeled nucleotides or PCR primers). Direct labeling schemes yield strong hybridization signals, typically using families of fluorescent dyes with similar chemical structures and characteristics, and are simple to implement. In preferred embodiments comprising direct labeling of nucleic acid targets, cyanine or alexa analogs are utilized in multiple-fluor comparative microarray analyses. In other embodiments, indirect labeling schemes are utilized to incorporate epitopes into the nucleic acid targets either prior to or after hybridization to the microarray probes. One or more staining procedures and reagents are used to label the hybridized complex (e.g., a fluorescent molecule that binds to the epitopes, thereby providing a fluorescent signal by virtue of the conjugation of dye molecule to the epitope of the hybridized species). In particular embodiments, a biotin epitope and a fluorescent streptavidin-phycoerythrin conjugate are contemplated. Another contemplated indirect labeling scheme employs the Tyramide Signal Amplification (TSA) procedure developed by NEN Life Science Products (Boston, Mass.). In particular, the TSA scheme utilizes biotin and dinitrophenol (DNP) epitopes as well as streptavidin and antibody conjugates linked to horseradish peroxidase (HRP) for labeling molecules of interest. In preferred embodiments, indirect labeling techniques provide 10 to 100-fold signal amplification relative to direct labeling approaches.

The present invention is not limited by the nature of the label chosen, including, but not limited to, labels which comprise a dye, fluorescein moiety, a biotin moiety, luminogenic, fluorogenic, phosphorescent, or fluors in combination with moieties that can suppress emission by fluorescence resonance energy transfer (FRET). Further, the probe oligonucleotide and particularly the target oligonucleotides may contain positively charged adducts (e.g., the Cy3 and Cy5 dyes, and the like). The oligonucleotides may be labeled with different labels (e.g., one or more probe oligonucleotides may each bear a different label).

It is also contemplated that similar sequences from different samples may be detected in a single microarray hybridization step. Material within different samples may be differently labeled. For example, targets within different samples may incorporate different dyes or fluorophores. When differently labeled in one of these ways, the contribution of each specific target sequence to hybridization at a particular probe site can be distinguished. This labeling scheme has several applications. In gene expression studies, for example, the relative rates of transcription of one or more particular sequences within a sample can be measured. Additionally, in some embodiments, the detection capabilities of the present invention can be used for detecting the quantities of different versions of a gene within a mixture. Different genes in a mixture to be detected and quantified may be wild type and mutant genes (e.g., as may be found in a tumor sample, such as a biopsy) or different genetic variants of microorganisms. In this embodiment, one might design two sets of one or more probes to be complementary to characteristic sequences in one region of the genome, but one probe set to match the wild-type sequence and one probe set to match the mutant. Quantitative detection of the fluorescence from a microarray reaction performed for a set amount of time will reveal the ratio of the two genes in the mixture. Such analysis may also be performed on unrelated genes in a mixture. This type of analysis is not intended to be limited to two genes. Many variants within a mixture may be similarly measured.

In still other embodiments, different sites on a single gene or sequence may be monitored and quantified by different probes to verify the presence of that gene or sequence. In this embodiment, the signal from each probe would be expected to be the same, or follow a characteristic intensity profile (i.e., providing confirmatory information).

It is also contemplated that multiple probes may be used that are similarly labeled upon hybridization, such that the aggregate signal is measured. This may be desirable when using many probes when identical or different sequences are used to detect a single gene or sequence to boost the signal from that gene. This configuration may also be used for detecting unrelated sequences within a mix.

The specificity of the detection reaction is influenced by the aggregate length of the target nucleic acid sequences involved in the hybridization of the complete set of the detection (probe) oligonucleotides. For example, there may be applications in which it is desirable to detect a single region within a complex genome. In other instances, it may be desirable to have the set of oligonucleotide probes interact with multiple sites within a particular sample target. In these cases, one approach would be to use a set of microarray elements that recognize a smaller, and thus statistically more common, segment of target nucleic acid sequence.

There exist many fluorescent indicators which operate in the dual excitation, single emission ratio mode; for example, Fura-2 and BTC for calcium and BCECF for pH. Multiple wavelength excitation also finds use when multiple single-excitation labels are used. Devices for switching between multiple excitation wavelengths from a broadband source include filter wheels and other mechanical devices (e.g., shutters, oscillating filters, etc.) and acousto-optics modulators or tunable filters. If a monochromatic light source is used (e.g., a laser or LED), it is contemplated that manual or automated switching between two or more light sources may be employed. Beamsplitters and/or moveable mirrors may, for example, be used to direct light with different excitation wavelengths into the optical system. The different excitation wavelengths may be utilized simultaneously or in a sequential manner.

The present invention contemplates a simple concordance test for determining the suitability of a particular dye or combination of dyes. The following test is useful in both direct and indirect multiemission (e.g., color) labeling schema. A single nucleic acid is labeled separately with one or more flours or epitopes and then hybridized to a single microarray. The fluorescent signals from all of the elements on the microarray are then determined at each particular emission wavelength. This data is then plotted as ratios as a function of signal intensity. Ideally, a ratio of 1.0 should be obtained for each labeled microarray element such that the data cluster tightly along the "sameness" line. Deviations from 1.0 suggest discordance or imbalance between the two channels that may be due to differences in incorporation or staining of the flours or epitopes, or to inaccuracies in detection and quantitation.

Examples of fluorophores suitable for labeling microarray samples include but are not limited to those found in Table 1 from "Microarray Biochip Technology" Schena et al., Eaton Publishing 2000.

| Fluorophore | Aprox. Absorbance (nm) | Aprox. Emission (nm) | Structural Partner | Comments |
|---|---|---|---|---|
| FITC† | 494 | 518 | | 5-FAM derivative used for DNA sequencing |
| Flour X | 494 | 520 | | Less bright than FITC |
| Alexa 488 | 495 | 520 | Alexa 432, 546, 568, and 594 | |
| Oregon Green 488 | 496 | 524 | | |
| JOE | 522 | 550 | | 6-JOE used for DNA sequencing |
| Alexa 532 | 531 | 554 | Alexa 488, 546, 568, and 594 | |
| Cy3 | 550 | 570 | Cy2, −3.5, −5, and −5.5 | |
| Alexa 546 | 556 | | Alexa 488, 532, 568, and 594 | |
| TMR‡ | 555 | 580 | | 6-TAMRA used for DNA sequencing |
| Alexa 568 | 578 | 603 | Alexa 488, 532, 546, and 594 | |
| ROX* | 580 | 605 | | 6-ROX used for DNA sequencing |
| Alexa 594 | 590 | 617 | Alexa 488, 532, 546, and 568 | |
| Texas Red | 595 | 615 | | |
| Bodipy 630/650 | 625 | 640 | Bopidy Series | |
| Cy5 | 649 | 670 | Cy2, −3, −3.5, and −5.5 | Less soluble in aqueous than Cy3 |

†fluorescein isothiocynate
‡tetramethylrhodamine
*X-rhodamine

IV. Exemplary System Configurations

Briefly, preferred embodiments of the present invention are described below comprising spatial light modulators that accept beams of collimated, or quasi-collimated, light from a light source and presents a pattern of light onto the surface of a substrate. In certain of these embodiments, the pattern of light presented to the surface of the substrate is computer-controlled. In the present invention, light presented to the substrate may be used for either or both of the steps of maskless microarray fabrication or detection of optical emissions (e.g., via exciting optically active molecules on the substrate surface and detecting optical emission therefrom including but not limited to emitted fluorescence). In preferred embodiments, optical emissions from the microarray substrate are directed to an emissions detector. In an alternative preferred embodiment, emissions from the substrate are returned through the excitation pathway such that the emissions are reflected back towards the excitation source through a beamsplitter which directs the emission to a detector. Fabrication and emission detecting functions can be conducted stepwise or simultaneously.

Alterations of the methods used for probe synthesis as described in WO/9942813 may be implemented to facilitate subsequent reading and hybridization of the microarrays. For example, during synthesis, some probe elements on the array may be left blank or with a sequence known to be unhybridizable to targets within the sample of interest. These reference sites may be used to enhance the signal to noise ratio of signals obtained using the detection methods as disclosed herein. Other embodiments of the present invention relate to fabricating microarray probe elements for use in monitoring the amount of analyte applied during hybridization. In these embodiments, a suboptimal, or less than complete, amount of light than is necessary for maximal photodeprotection of the combinatorial reagents and chemicals is directed at a subset of sites on the microarray. For example, of the light directed to the microarray substrate via a spatial light modulator a subset of those beams may be momentarily or periodically diverted from striking the microarray substrate such that one or more sites on the microarray receive less light than neighboring sites (e.g., via control of the spatial light modulator such that one or more particular sites on the microarray substrate receives less light energy for interacting with photolabile reagents at that site). It is contemplated that the subset of sites on the microarray affected in this manner comprise varied probe molecules such that relatively non-specific hybridization may occur at the site as a whole. Sites produced with this "randomization" procedure may be used to monitor the level of analyte applied to the microarray during hybridization steps.

In the configuration shown in FIG. 1, an output beam 24 is emitted from a light source assembly 20 and passes through one or more wavelength selectors 22 on its path to the spatial light modulator 26. The light source assembly 20 may be a lamp housing (e.g., Model # 66921, Oriel Instruments, Stratford, Conn.) that accommodates a lamp, reflector, condenser, and any number of beam conditioning accessories known to the art. In some embodiments, the light source 20 comprises a polychromatic lamp, for example, the light source 20 may comprise a mercury or xenon arc lamp, mercury-xenon arc lamp, xenon flash lamp, or other ultraviolet or near ultra violet light source (e.g., an Oriel 1,000 W Hg arc lamp, model 6287, Oriel Instruments, Stratford, Conn.). In other embodiments, the light source 20 comprises a metal-halide or incandescent lamp, a laser, or light emitting diodes (LEDs). Additionally, in some embodiments, light source 20 comprises a dichroic beam turner (e.g., Model #66228, Oriel Instruments, Stratford, Conn.) and/or a liquid filter (e.g., Model # 6127, Oriel Instruments, Stratford, Conn.) to eliminate infrared light from the output beam 24. Preferably, infrared blocking filters are chosen to minimize heat build-up in downstream optical devices of the system while allowing ultraviolet and fluorescent excitation light to be transmitted. In preferred embodiments, a condensing lens 21 assembly is mounted within or near the light source 20 and provides collimation to output beam 24. In other embodiments, a light pipe scrambler or additional collimating optics (not shown) may be employed to improve output beam 24 uniformity (e.g., a Kohler illuminator). In still further embodiments, the output beam 24 may be coupled into a quartz fiber or liquid light guide (not shown) for the purpose of remotely locating the light source 20 from the rest of the system. This is known to mitigate vibration from the light source 20 housing fans as well as electromagnetic interference from light source 20.

In preferred embodiments, wavelength selector 22 is a passband filter which further narrows the spectra of beam 24 by transmitting only a narrow (e.g., 10 nm-60 nm) band of wavelengths. Wavelength selector 22 may comprise a combination of one or more light collimating lenses and monochromating devices (e.g., diffraction gratings, linearly variable interference filters, tunable ferroelectric filters, prisms, and the like). In particularly preferred embodiments, wavelength selector 22 comprises a filter wheel. Such filter wheels are commercially available and comprise one or more colored optical materials or interference passband filters mounted in a rotatable carriage. Individual passbands can be selected by manually turning the filter wheel, or by a motor controlled by CPU 60. For microarray synthesis, wavelength selector 22 is directed (e.g., by rotating a filter wheel) to select a filter (e.g., Model# 56531 Oriel Instruments, Stratford, Conn.) that allows light suitable for light-directed microarray synthesis (e.g., a 10 nm band surrounding the 365 nm mercury spectral line). Wavelength selector 22 may also contain one or more interference filters (e.g., Model# XF1074, Omega Optical Inc, Brattleboro, Vt.), each with a passband centered on the excitation wavelength of an optically active marker (e.g., a fluorescent label). In a preferred detection embodiment, these filters are also selectable by wavelength selector 22 (e.g., by including said filters in a rotatable filter wheel). Regardless of the wavelength being emitted, the cross-section of the output beam 24 should be large enough to illuminate the entire active surface of the spatial light modulator 26.

After passing through the elements 21 and 22, output beam 24 is projected onto spatial light modulator 26. In preferred embodiments, the spatial light modulator 26 comprises a microelectrical mechanical system capable of redirecting portions of a collimated beam of light falling upon its surface. One such microelectrical mechanical system is a micromirror array, such as a Digital Micromirror Device (DMD). In some embodiments where the spatial light modulator 26 is a micromirror array, the array comprises a two-dimensional arrangement of individual micromirrors 27 each of which are responsive to control signals supplied to the array device 26 to tilt in one of at least two directions. In particular, individual micromirrors 27 associated with micromirror control circuitry 66 are actuated in response to digital control signals from CPU 60. The micromirror 27 is constructed so that in a first position (i.e., "on" position), the portion of the incoming beam of light 24 that strikes an individual micromirror 27 is deflected in a direction oblique to the incoming beam 24, as indicated by light beam 28. In a second position (i.e., "off" position), the light from output beam 24 striking such mirror in such second position is reflected as a beam 30 at such incidence to either strike light absorber 32, or to exit the system without interference.

A preferred DMD is available commercially from Texas Instruments, Inc. These devices have arrays of micromirrors (each of which is substantially a square with edges of 10 to 20 mm in length) that are capable of forming patterned beams of light by electronically addressing the micromirrors in the arrays. Such DMD devices are typically used for video projection and are available in various array sizes, e.g., 600×800 (SVGA; 480,000 pixels), and 1024×768 (XGA; 786,432 pixels). Such arrays are discussed in the following article and patents: Larry J. Hornbeck, "Digital Light Processing High-Brightness, High-Resolution applications," World wide Web site://www.ti.com/dlp; and U.S. Pat. Nos. 5,096,279; 5,535,047; 5,583,688; and 5,600,383 (herein incorporated by reference in their entireties). The micromirrors 27 of such devices are capable of reflecting the light of normal usable wavelengths, including ultraviolet and near ultraviolet light, in an efficient manner without damage to the mirrors themselves. In some embodiments, the window of the enclosure for the micromirror array preferably has anti-reflective coatings thereon optimized for the wavelengths of light being used. Typical micromirror device dimensions of 16 microns per mirror side with a space of 1 micron between mirrors gives a mirror element array pitch of 17 microns. Commercially available 1024×768 arrays of micromirrors with 786,432 independently controlled micromirrors have active array dimensions of 17.4 millimeters by 13.1 millimeters.

The light reflected from the spatial light modulator 26 by the micromirrors 27 when in the "on" position constitutes a plurality of individual beams 28. In preferred embodiments, the plurality of beams 28 are collected by an optical relay system 34. In preferred embodiments, the optical relay system 34 comprises a spherical concave mirror 35 that reflects the plurality of beams of 28 onto a spherical convex mirror 36, which in turn redirects the plurality of beams 28 back to the spherical concave mirror 35 and exits the optical relay system 34. An advantage of this type of reflective projector is that it can image a broad wavelength range with very low aberration. Suitable spherical concave mirrors 35 are available with ultraviolet enhanced coatings (e.g., Model #43-561, Edmund Scientific, Barrington, N.J.). The convex mirror 36 may be fabricated by coating a small convex lens (e.g., Model #45-625, Edmund Scientific, Barrington, N.J.) with a reflective coating using standard thin-film techniques. Ideally, the radius of curvature of the convex mirror 36 is half that of the concave mirror 35. In preferred embodiments, the centers of curvature of the convex and concave mirrors are coincident in the plane of image formation, with the spatial light modulator and active surface of the microarray situated equidistant from this center of curvature. In preferred embodiments, of the present invention, optical relay system 34, when comprising optical components 35 and 36 comprises an Offner Relay. One skilled in the art, in view of the present disclosure, will readily appreciate the design and application of Offner style optical relays within the operation of the present invention (See e.g., U.S. Pat. No. 4,011,011 [herein incorporated by reference in its entirety]; Schafer, Applied Optics 17(7);1072 [1978]; Ih and Yen, Applied Optics 19(24):4196 [1980]; and Murty, Optical Engineering 24(2):326 [1985]). Alternative embodiments of, apperatures (i.e., to limit the angles of light accepted by optical rely system 34), lenses, filters, and mirrors are contemplated as optical relay systems 34 for use in the present invention, so long as the optical pattern produced by the spatial light modulator 26 is imaged onto the active surface of the microarray substrate 38. Those skilled in the art will also appreciate that alternative configurations are contemplated, such that the relative order of the optical elements in the light path is varied. For example, in some embodiments, the wavelength selector 22 may be placed after the optical relay system 34, allowing a composite filter mount to be employed. Certain other embodiments, employ a "filter cube" that incorporates excitation and emission filters matched to a particular label, thereby facilitating manual exchange and alignment of said filters for use with different experimental protocols.

The plurality of individual light beams 28 exiting the optical relay system 34, strike beamsplitter 43. In some embodiments, this element my comprise a longpass dichroic beamsplitter with a transition wavelength between the excitation and emission bands of the fluorescent label of interest (e.g., Model# XF2017 Omega Optical Inc, Brattleboro, Vt.). The beamsplitter 43 serves to direct the image light beams 29 towards the microarray substrate 38, while preserving the imaging capability of the optical relay system 34 for selected wavelengths. In preferred embodiments, the microarray substrate 38 is transparent and is enclosed in flow cell chamber 40 (e.g., Model #49, NSG Inc, Farmingdale, N.Y., Model# H-18210, Molecular Probes Inc. Eugene, Oreg.). In a preferred embodiment, the microarray is fabricated on a glass slide associated with a flow cell chamber 40. In preferred embodiments, suitable flow cell chambers 40 comprise a flow cell volume bounded by the glass slide, an adhesive gasket and a coverslip. The flow cell volume defines a preferred hybridization chamber when outfitted with an inlet 41 and outlet 42 for sample and reagent delivery. While a flow cell chamber 40 inlet 41 and outlet 42 are described in some embodiments, the present invention is not intended to be limited to employing any particular arrangement or number of portals to the flow cell chamber 40. The flow cell chamber 40 is preferably designed to have a minimal volume so as to reduce reagent usage. In preferred embodiments, flow cell chamber 40 may comprises a first glass slide (array substrate) associated with a second glass slide wherein a suitable gasket is positioned between the slides so as to form a chamber. In some embodiments, the flow cell chamber 40 comprises, in any orientation, an inlet port 41 and outlet port 42 such that reagents are deliverable to microarray substrate 38. In some other embodiments, the flow cell chamber 40 comprises a ported housing, an inert liner, and a clamping mechanism for physical registration and sealing of a glass substrate. In a preferred embodiment, the flow cell housing may be thermally controlled. Suitable systems for regulating temperature are well known and may comprise a sensor, thermoelectric device (heats and cools) and a feedback controller, among other devices.

Additionally, flow cell chamber 40 comprises one or more transparent surfaces such that microarray substrate 38 is optically accessible from one or more of the surfaces of the assembly. In some preferred embodiments, flow cell chamber 40 comprises an inlet tubing 71 and outlet tubing 72. The position of tubing 71 and 72 as depicted in FIG. 1 are associated with flow cell chamber 40 in one of several contemplated embodiments. For example, in some embodiments, tubing 71 and 72 may both enter the flow cell chamber 40 from a position oblique the microarray substrate 38. In an alternative embodiment, tubing 71 and 72 are associated with one or more additional tubings for delivering or purging the combinatorial chemicals and detection probes and reagents used in microarray fabrication and detection operations. In still another embodiment, tubings 71 and 72 are replaced by one tubing for both delivering and purging the combinatorial chemicals from flow cell chamber 40. In preferred embodiments, flow cell chamber 40 is attached, as described in the various embodiments, via tubing to a device known as a DNA synthesizer (e.g., Labtronics, Inc., Monroe, Oreg.; PE Biosystems, Foster City, Calif.). Alternatively, the flow cell chamber 40 is attached via tubing to one or more devices that supply combinatorial chemicals (e.g., photolabile protecting molecules, nucleotides, amino acids, peptides, and the like, flow cell chamber wash solutions, hybridization targets, labeling molecules, and the like).

Some embodiments of the systems and devices of the present invention are employed for fabricating patterned microarray features on microarray substrates 38. In certain of these embodiments, the flow cell chamber 40 is associated with the microarray substrate 38 such that the disclosed systems and devices operate to fabricate patterned microarray features using the maskless combinatorial chemistry techniques described in PCT publication WO/9942813 (incorporated herein by reference in its entirety). In a preferred embodiment of the present invention, deoxyribonucleic microarray features are fabricated on the microarray substrates 38 as adaptations of microlithographic techniques. In one embodiment of a "direct photofabrication approach," the microarray substrate 38 is coated with a layer of a chemical capable of binding the nucleotide bases (e.g., silane). Filtered ultraviolet light is supplied by the light source 20 and wavelength selector 22 and directed to the spatial light modulator 26. The pattern of light defined by "on" elements of the spatial light modulator 26 is imaged onto the active surface of the microarray substrate 38 by the optical relay system 34 and the beamsplitter 43. Areas on the substrate 38 that correspond to "on" elements of the spatial light modulator 26 will receive ultraviolet light, thereby deprotecting OH groups on the substrate and making them available for binding the nucleotide bases. During exposure, the appropriate nucleotide base is flowed onto the surface of the microarray substrate 38 via the flow cell chamber 40 such that nucleotides bind to the selected sites using normal phosphoramidite DNA synthesis chemistry. In preferred embodiments, this process is repeated, under programmed control, with the CPU 60 controlling the pattern of the micromirrors for each nucleotide base addition step. The process is simple, yet can yield exponential combinatorial complexity for a linear number of synthesis steps. In other embodiments, the molecular synthesis methods based on photoresist technology are employed for microarray fabrication (See e.g., McGall, et al., Proc. Natl. Acad. Sci. USA 93:13555 [1996]; and McGall, et al., J. Amer. Chem. Soc. 119(22):5081 [1997]). In the indirect photofabrication approach, compatible chemistries exist with a two-layer resist system, where a first layer of, e.g., polyimide acts as a protection for the underlying chemistry, while the top imaging resist is an epoxy-based system. The imaging step is common to both synthesis processes, with the main requirement being that the wavelength of light used in the imaging process be long enough not to excite transitions (chemical changes) in the molecules being synthesized. Nucleotide bases are particularly sensitive at 280 nm, hence, wavelengths longer than 300 nm should be used for oligonucleotide synthesis.

In one particular embodiment, microarray probe elements are fabricated on a microarray substrate 38 according to the method described by Gasson et al., Nature Biotechnology 17:974 (1999), hybridized with labeled targets, excited and read with the system and device described herein.

In some embodiments, microarrays are not synthesized using the system of the present invention but are provided, pre-manufactured, from a different source. In such cases, the microarrays obtained may be manufactured to correspond to the spatial light modulator 26 of the present invention (i.e., probe elements spatially correspond to specific micromirrors). In some embodiments, the projection magnification ratio may be adjusted to accommodate different element sizes and spacings (pitch). In either case, the microarray elements should have the same X/Y pitch ratio as the spatial light modulator 26. Additionally, microarray elements with the proper pitch ratio can be much larger than the spatial light modulator elements so long as the magnification ratio of the projection optics results in a correspondence to integral numbers of spatial light modulator elements. Given this, any microarray can be mounted, physically registered, and then analyzed by the present invention so long as its analysis requires detection from an equal or lesser number of elements in a given direction than the number of spatial light modulator elements in a corresponding direction. For analyzing microarrays that are synthesized according to the present invention, registration is automatic and inherently accurate. After synthesis, the microarray may remain mounted in the synthesizer/analyzer for hybridization or analysis. This aspect of the preferred embodiments disclosed herein are advantageous in terms of accuracy, repeatability and speed of operation. The combination of synthesis and analysis functions also greatly facilitates automation of many procedural steps that would otherwise require human action.

The present invention contemplates a number of detection schemes. For example, in a preferred embodiment, as depicted in FIG. 1, optically active molecules (e.g., fluorescent labels) bound to probes on the microarray substrate 38 emit characteristic optically detectable emission light 45 when the probes are selectively excited by the image light beams 29. In this mode of operation the spatial light modulator is used as an excitation mask. A portion of emission light 45 passes through beamsplitter 43 and is collected by detector collection optics 44. In preferred embodiments, an emission filter 46 (e.g., Model #XF3085, Omega Optical Inc, Brattleboro, Vt.) serves to attenuate any non-extinguished excitation light, as well as light from background fluorescence. Optically detectable emission signals 45 emitted from excited labels on any or all of the probe sites on the microarray substrate 38 are detected by photodetector 48. In certain of these embodiments, the photodetector 48 comprises a channel photomultiplier tube (e.g., PE 944p, Perkin-Elmer Optoelectronics, Santa Clara, Calif.). The photodetector 48 provides an electronic signal 49 to the data acquisition system 56 (described below) which generates data for manipulation and storage by the CPU 60 (e.g., Model# CMM7686-GX-233-128, Real Time Devices, State College, Pa.). It is contemplated that photodetector 48 could be located in a number of positions and still function to receive emission light from the microarray. For example, the photodetector 48, detector collection optics 44, and emission filter 46 could all be situated to gather emission light from the opposite side of a transparent flow cell, in which case the redirection of the excitation pattern 29 by beamsplitter 43 is not needed. The photodetector 48 provides an electronic signal 49 to the data acquisition means 56 (described below) which generates data for storage by the CPU 60 and/or communication through an I/O channel 68 (described below). In preferred embodiments, the CPU 60 is in bi-directional operable communication 62 and 58 with the data acquisition means 56 (described below). Additionally, in preferred embodiments, CPU 60 communicates operably 65 with spatial light modulator driver 66 such that the individual mirrors 27, when the spatial light modulator is a DMD, of the spatial light modulator 26 are actuated through "on" and "off" positions (described below).

Figure 2:
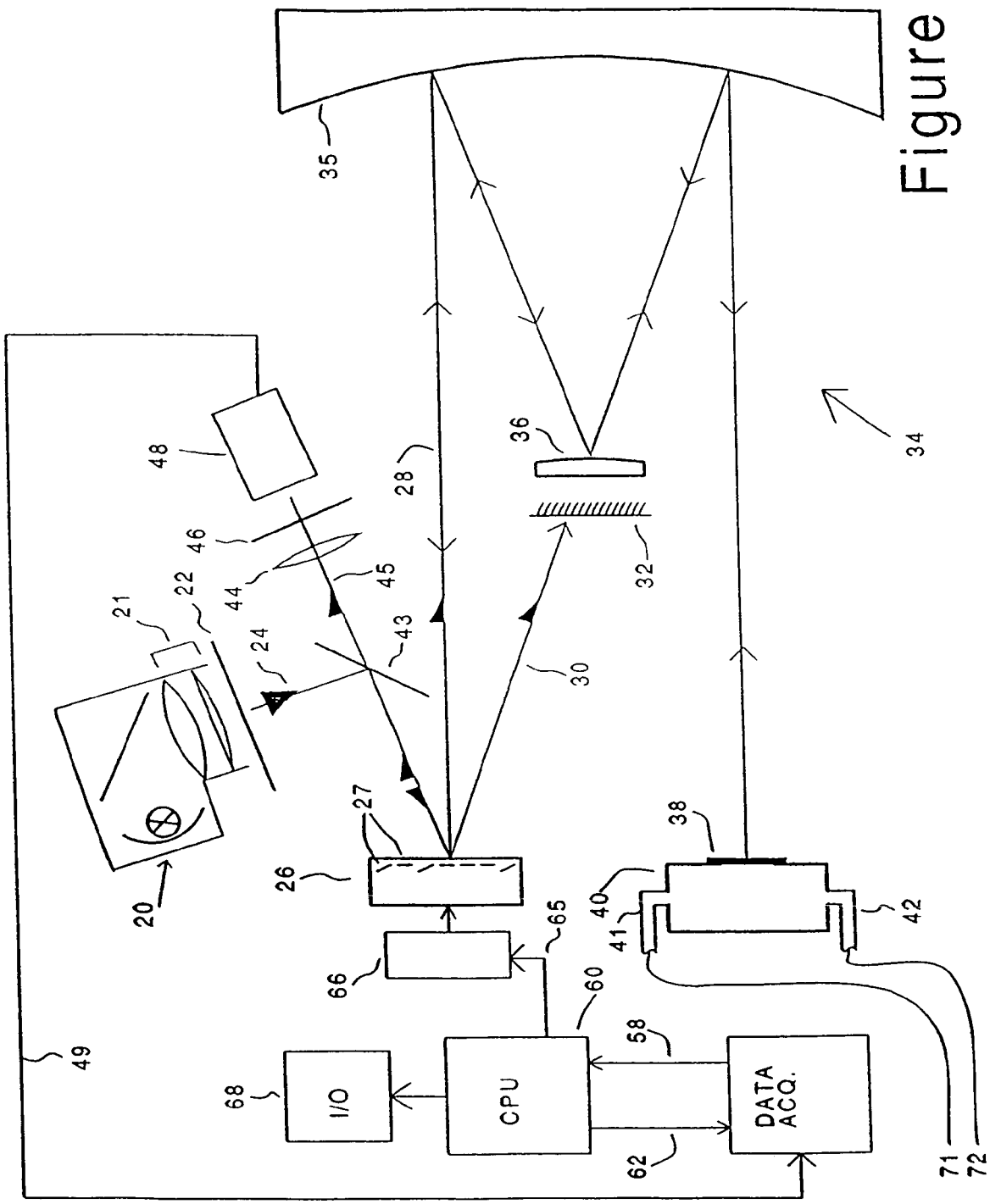
FIG. 2 shows a system using a micromirror spatial light modulator.

An alternative embodiment, depicted in FIG. 2, provides for the use of non-fluorescent labels. If chemiluminescent or bioluminescent labels are used, the light source 20 is turned off, diverted, or removed. The photodetector 48 is positioned such that the characteristic optically detectable emissions signals 45 from excited optically labeled molecules on microarray substrate 38 are returned through the device via the optical components described herein, such that the emissions are collected by the spherical concave mirror 35 and are directed to the spherical convex mirror 36 and then back again to the spherical concave mirror 35 and onto the spatial light modulator 26 which exactly reflects the particular emissions from discrete microarray elements to the beamsplitter 43. In this configuration, the spatial light modulator functions as an emission mask when used with nonexcited (e.g. chemiluminescent) labels. If fluorescent labels are used, the spatial light modulator functions as both an excitation mask and emission mask. In these embodiments, beamsplitter 43 directs the emitted light through one or more detector collection optics 44 and through emission filter 46 before photodetector 48. In some embodiments, emission filter 46 is a passband filter.

In some of the embodiments of the present invention, depicted in FIG. 2, the spatial light modulator 26 further comprises a transmissive spatial light modulator (e.g., an LCD provided with back illumination). In some of these embodiments, the spatial light modulator 26 further comprises a reflective spatial light modulator. It is contemplated that the alternative embodiments of the spatial light modulator 26 described above allow either excitation masks or emissions masks to be employed in the operation of the present invention. Moreover, those skilled in the art will appreciate modifications necessary to the embodiments recited in FIG. 2 for employing either transmissive spatial light modulators or reflective spatial light modulators in the present invention.

Figure 3:
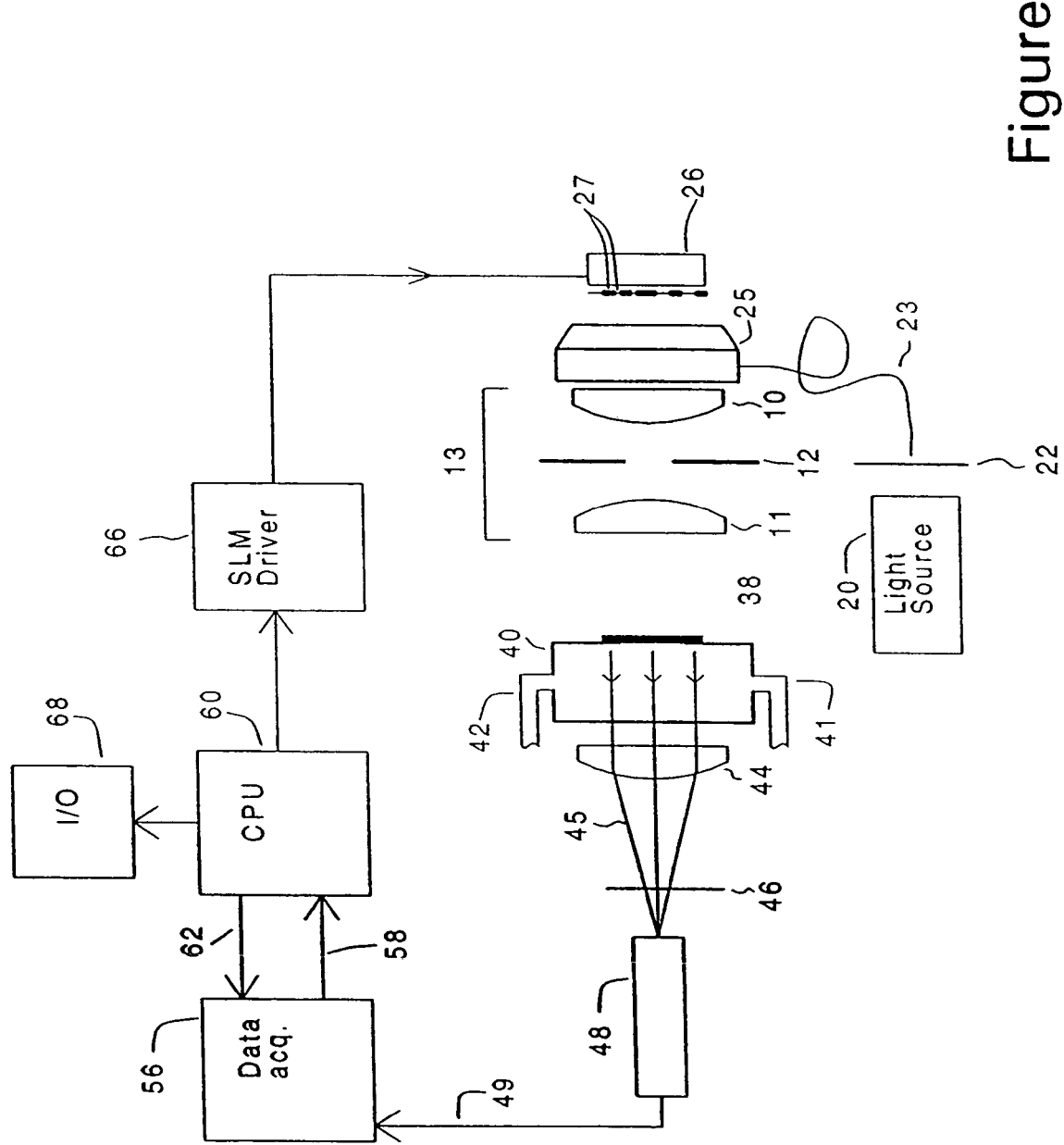
FIG. 3 shows a system using FLCD spatial light modulator.

Another embodiment of the present invention is shown in FIG. 3 comprising a spatial light modulator, a photodetector, and a light source. It is contemplated that this embodiment is particularly useful for hybridizing and/or reading microarrays that have been produced by the synthesis methods described above or by other equipment. In preferred embodiments depicted, fluorescent labelling is used (e.g. Alexa Fluor 546, Molecular Probes Inc. Eugene, Oreg.).

In a preferred embodiment, light source 20 produces an output beam of light that optionally passes through a wavelength selector 22 prior to entering fiber optic cable 23. The output beam directed through fiber optic cable 23 enters a fiber optic ring illuminator 25 (e.g. Model# 54-175, Edmund Industrial Optics, Barrington, N.J.). The fiber optic ring illuminator 25 provides a source of uniform excitation light to the spatial light modulator 26. In a preferred embodiment, wavelength selector 22 comprises a bandpass excitation filter (e.g., Model# XF1074, Omega Optical Inc, Brattleboro, Vt.) with a center wavelength chosen to match the excitation wavelength of the fluorescent label being detected. In some embodiments, light source 20 comprises a polychromatic light source (e.g., Dolan-Jenner model #PL-900). Alternatively, light source 20 comprises a monochromatic light source such as one or more LEDs or lasers. In a preferred embodiment, light source 20 and fiber optic ring illuminator 25 provide uniform illumination of the spatial light modulator 26. In a preferred embodiment, spatial light modulator 26 comprises a Ferroelectric Liquid Crystal Display panel (FLCD) (e.g., Model LDP-0307-MVI, Displaytech, Longmont Colo.). In these particular embodiments, the FLCD (8.32 mm×6.24 mm) reflective display comprises a ferroelectric liquid crystal applied to a CMOS integrated circuit. The FLCD preferentially comprises an two-dimensional array of 640×480 on-board liquid crystal light modulation elements on a planar reflective surface. These modulation elements act like shutters above a mirror and can be individually controlled by spatial light modulator driver 66 to be in either a reflective ("on") or non-reflective ("off") state.

Light from the fiber optic ring illuminator 25 that is received by "on" elements of the spatial light modulator 26 is reflected through the open body of the fiber optic ring illuminator 25 to a refractive optic projector 13. In this embodiment, the spatial light modulator functions as an excitation mask. In preferred embodiments, the refractive optics projector 13 is of standard relay design (e.g., Model #46-007, Edmund Industrial Optics, Barrington N.J.) and images the light from the "on" pixels of the spatial light modulator to their associated probe elements on the microarray substrate 38. Refractive optics projector 13 typically comprises, although other embodiments are contemplated, lenses 10 and 11. Lenses 10 and 11 can have the same or different focal lengths, and may be selected to provide enlargement or reduction so as to match different microarray probe element pitches. In some embodiments, the refractive optic projector 13 further comprises an aperture 12 that can be adjusted to optimize resolution versus optical throughput. The rationally selected pattern of light spots projected onto the microarray substrate 38 determines which microarray probe elements are optically excited and thus which elements will emit emission signals 45.

In preferred embodiments, emission signals 45 exit the flow cell chamber 40 opposite the microarray substrate 38 and are directed through the detector collection optics 44 and emission filter 46 before striking photodetector 48. In some embodiments, emission filter 46 is a passband filter. In particularly preferred embodiments, detector collection optics 44 comprises optics (e.g., a lens) with an F# sufficient to image the whole active area of the microarray substrate 38 onto the active area of the photodetector 48. Emission filter 46 (e.g., Model# XF3085, Omega Optical Inc, Brattleboro, Vt.) is chosen to preferably transmit the emission wavelength of the label(s) of interest and to exclude excitation light. Photodetector 48 may be a photomultiplier (e.g., PE 944p, Perkin-Elmer Optoelectronics, Santa Clara, Calif.). The signal 49 from photodetector 48 signal is received by data acquisition system 56 and CPU 60.

Figure 4:
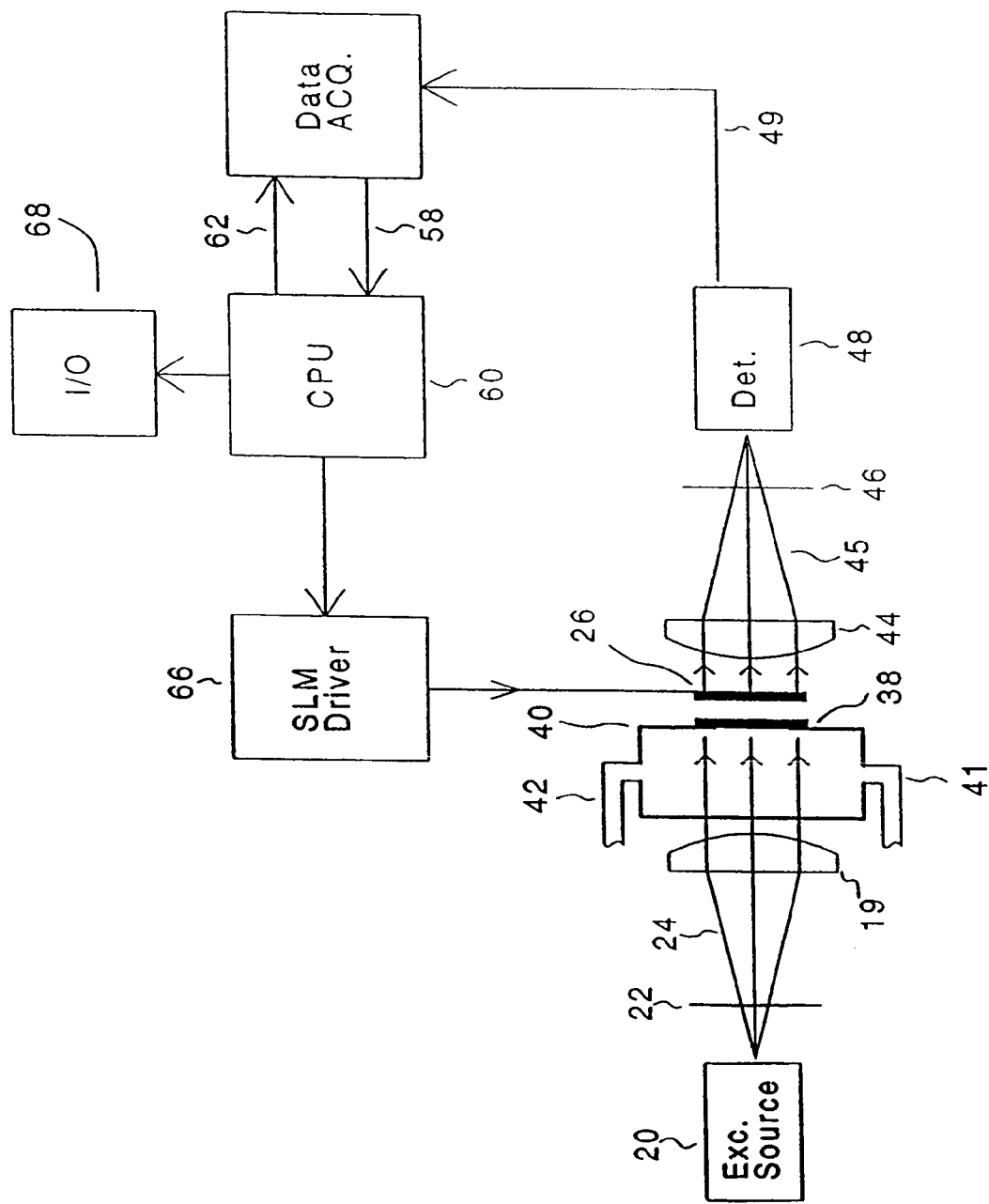
FIG. 4 shows a system comprising a transmissive spatial light modulator.

In still another embodiment of the present invention, the systems and devices comprise a transmissive spatial light modulator, a photodetector, and an optional light source as shown in FIG. 4. It is contemplated that the embodiments depicted in FIG. 4 will be useful for hybridizing and/or analyzing microarrays that have been produced by other means and systems. In certain of these embodiments, when chemiluminescent or bioluminescent labels are used, the light source 20 is turned off, diverted, or removed. In preferred embodiments, fluorescent labelling is used (e.g., Alexa Fluor 546, Molecular Probes Inc. Eugene, Oreg.) and the entire microarray is provided with one or more wavelengths of excitation suitable to excite the fluorescent labels selected by light source 20. In some embodiments, a fiber optic light guide (not shown) is provided to direct the output light 24 to the flow cell chamber 40. In preferred embodiments, output light 24 is directed through a wavelength selector 22 before passing through collimating optics 19. The light source may be a polychromatic illuminator (e.g., Dolan-Jenner model #PL-900). Alternatively, a monochromatic light source such as an LED or laser may be used for excitation. In preferred embodiments, the source provides uniform illumination of the array 38. In preferred embodiments, wavelength selector 22 comprises one or more bandpass excitation filters (e.g., Model# XF1074, Omega Optical Inc, Brattleboro, Vt.) with a center wavelength chosen to match the excitation wavelength of the fluorescent label being detected.

In preferred embodiments, output light 24 passes through the posterior surface of flow cell chamber 40 and exits the microarray substrate 38 before striking spatial light modulator 26 as emission light 45. Preferably, the microarray substrate 28 is closely located parallel to, and registered with, the spatial light modulator 26 (i.e., probe elements corresponding spatially with spatial light modulator elements). In preferred embodiments, the spatial light modulator 26 comprises a two-dimensional array of selectively opaque or transmissive elements (e.g., a liquid crystal device "LCD"). Thus, each spatial light modulator 26 element acts as a shutter controlled by CPU 60 that corresponds to a particular probe element on the microarray substrate 38. In this configuration, the spatial light modulator is used as an emission mask. When the present invention is configured in this manner, the spatial light modulator 26 permits rationally selected emission light 45 beams to pass to photodetector 48. Emission light 45 emanating from a labelled probe sites on the microarray substrate 38 are detectable only if their corresponding spatial light modulator 26 element is in a transmissive state. Thus, spatial light modulators in these embodiments can be referred to as emission masks. Since visible light is used in certain read-only configurations, liquid crystal devices of the type used for displaying small graphic images are suitable as spatial light modulators in certain of these embodiments. These devices are widely known in the art and are available from Seiko, Epson and other companies. In preferred embodiments, emission light 45 is collected from the output side of the spatial light modulator 26 by a detection collector optics 44. This assembly may comprise one or more elements to provide an effective F# sufficient to concentrate light from the whole active area of the spatial light modulator onto the active area of the photodetector. Optionally, an emission filter 46 (e.g., Model# XF3085, Omega Optical Inc, Brattleboro, Vt.) is chosen to preferably transmit the emission wavelength of the label(s) of interest. In some preferred embodiments, emission filter 46 comprises a passband filter. Typically, the photodetector 48 is positioned to receive emission light 45 emanating from rationally selected probe sites on microarray substrate 38. In preferred embodiments, photodetector 48 may be a photomultiplier (e.g., PE 944p, Perkin-Elmer Optoelectronics, Santa Clara, Calif.).

In FIG. 1-3 the CPU 60 controls both the spatial light modulator 26 and the data acquisition system 56 (through control path 62) and can therefore synchronize acquisition of emission signals 45 from photodetector 48 with the optical excitation patterns provided to the microarray substrate 38. In the embodiment shown in FIG. 4, an emission mask pattern is generated instead of an excitation pattern. The synchronization between the data acquisition system 56 and the selective optical interrogation of the microarray is important to the operation of the microarray analyzer as disclosed herein in certain embodiments. The data points acquired in this way are in the form of one emission value per optical interrogation pattern. This data is presented to the CPU 60 by signal path 58.

Figure 5:
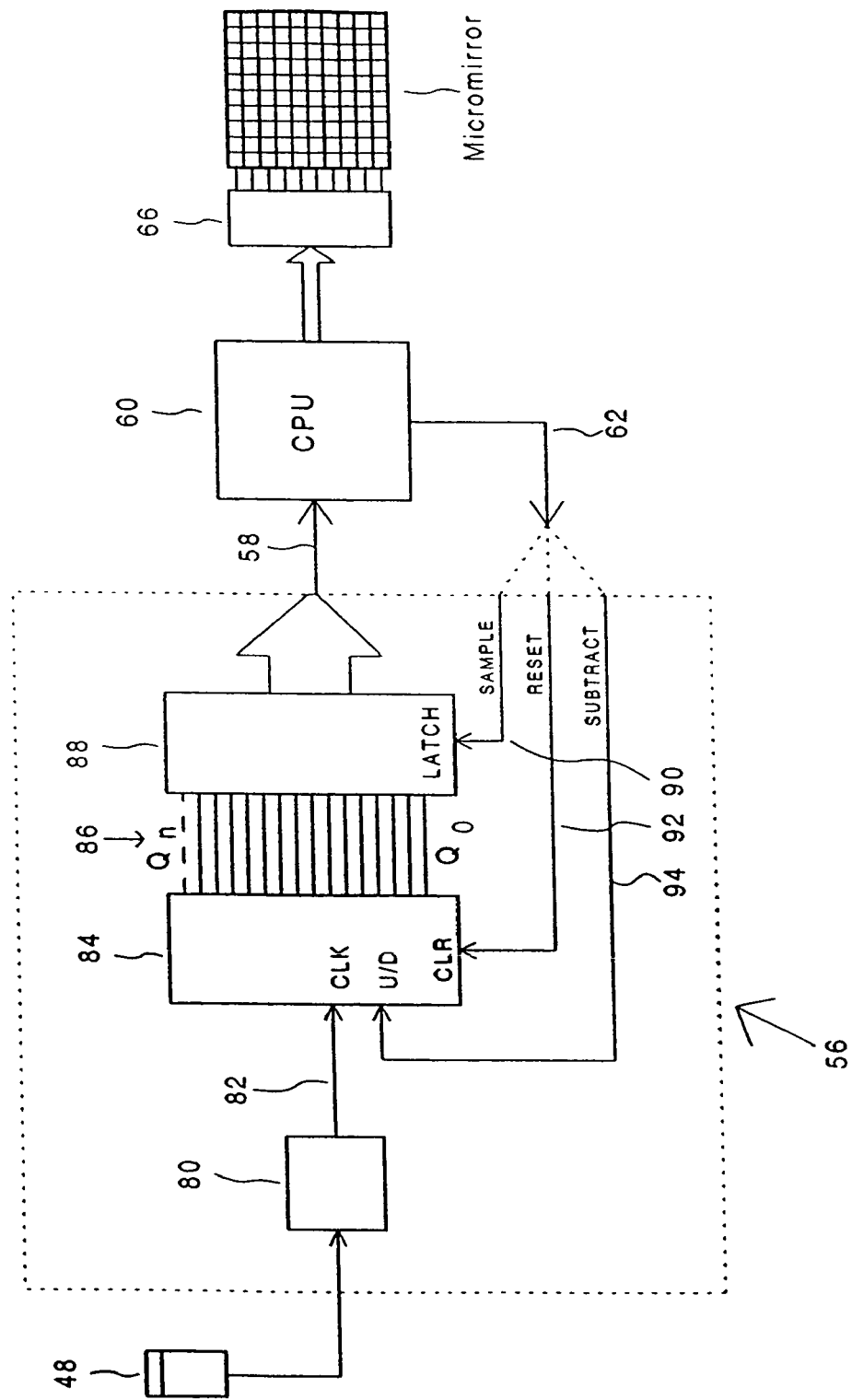
FIG. 5 shows a schematic of a photon counting data acquisition system.

FIG. 5 shows a block diagram of a preferred data acquisition system. In some embodiments, the photodetector 48 is a channel photomultiplier (e.g., PE 944p, Perkin-Elmer Optoelectronics, Santa Clara, Calif.) operated in photon counting mode. This mode of operation relies on relatively high biasing of the photomultiplier to create a detectable pulse for each photon that strikes the photocathode. Certain embodiments of the present invention comprise, an amplifier-discriminator 80 that may be of standard design (e.g., Model #AD5, Electron Tubes, Inc., Rockaway, N.J.) that serves to invert and amplify the small current pulses 49 from the photodetector 48 into TTL level voltage pulses on signal path 82 that have a fixed pulse width of about 25 ns. In still other preferred embodiments, the present invention further comprises an up/down counter 84 (e.g., a fast hardware or software counter with up/down control). Certain of these embodiments, utilize four cascaded synchronous up/down 4-bit counters (e.g., 4×74ACT169) to provide a 16 bit maximum count. The up/down counter 84 provides a 16 bit parallel binary signal 86 to the output register 88 that represents the number of photons that have been detected by photodetector 48 since the up/down counter 84 was last reset by the CPU 60 via assertion of control line 92 (RESET). The photon count increments upward as long as the (SUBTRACT) line is not asserted. The photon count is preferably transferred to an input port 58 of CPU 60 by assertion of control line 90 (SAMPLE) by the CPU. The time between the (RESET) and (SAMPLE) assertions by the CPU 60 is the time period over which photons are integrated. Longer integration times can be provided under software control to effect a higher "gain" for low-level signals. This may be determined by programmed iteration of the (SAMPLE) cycle. This capability increases the effective dynamic range of the system while retaining faster sampling rates when detecting higher emission levels. This is particularly advantageous in the present invention, where differing numbers of probe sites may be interrogated during analysis of a particular microarray.

Figure 6:
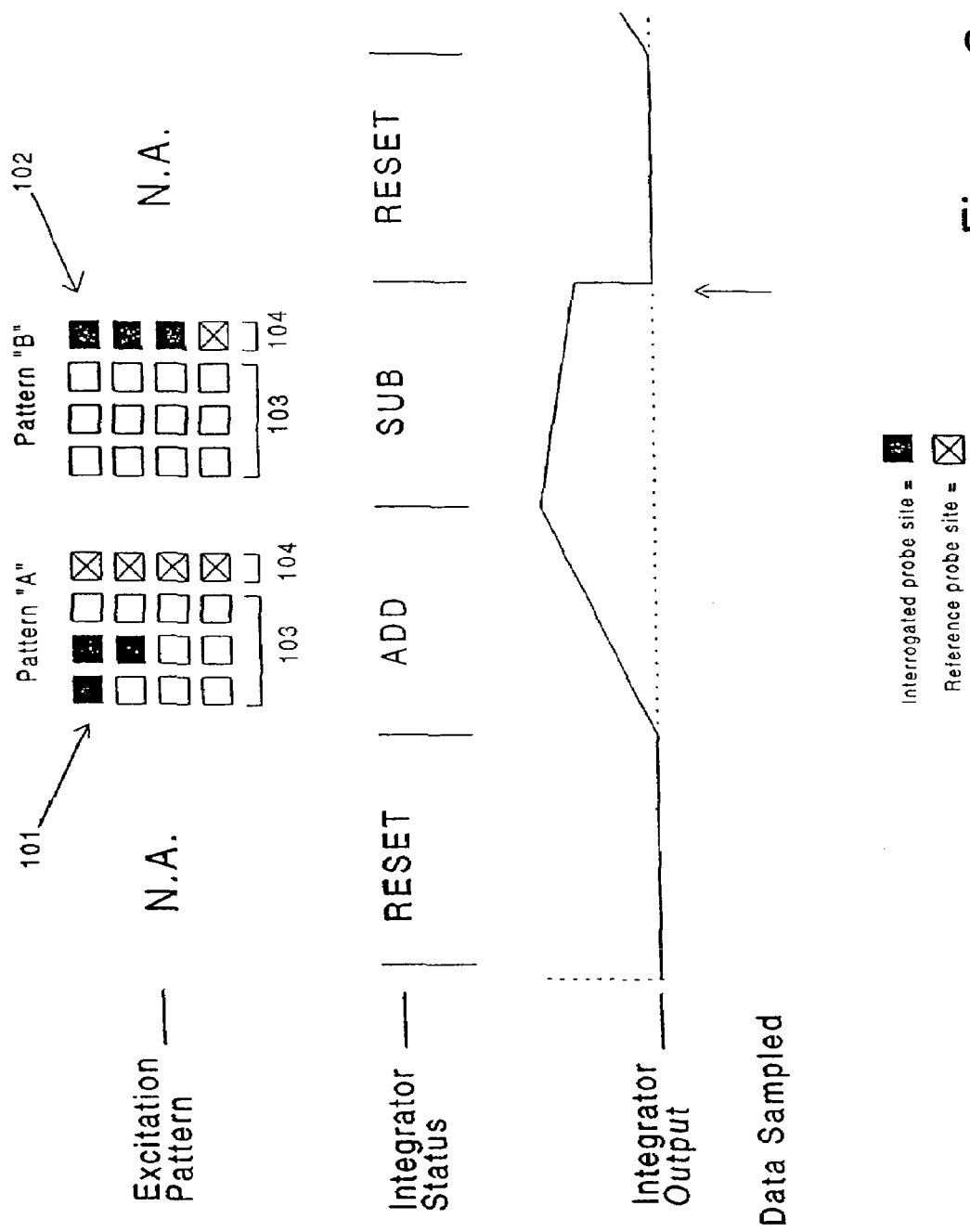
FIG. 6 illustrates the coordination of a spatial light modulator with a data acquisition system in one embodiment of the present inveniton.

The up/down counter 84 may also be commanded by the CPU 60 to count downward from a previous count by assertion of control line 94 (SUBTRACT). This results in further photon pulses being subtracted from any previous count. FIG. 6 illustrates the synchronous operation of the data acquisition system in concert with two different interrogation patterns supplied to the same microarray probe elements by the spatial light modulator. The following programmed CPU 60 control sequence is shown:

RESET; Integrate PATTERN "A" with (NOT SUBTRACT); Integrate PATTERN "B" with SUBTRACT; SAMPLE.

These operations result in the CPU 60 acquiring data that represents the difference between the emission signals due to interrogation patterns "A" 101 and "B" 102. It is contemplated that the above subtraction function may be instead implemented in the control software by always integrating additively before sampling and then comparing the results in a software register. It is useful, however, to illustrate the ability of the present invention to subtract one emission signal from another, as it has important consequences in terms of increasing the signal to noise ratio.

In preferred embodiments, the signal to noise ratio associated with a single interrogation pattern may be limited by various noise sources which are relatively constant in amplitude over time and between one microarray element and another. These include detector noise, system noise, and background artifacts. By comparing the emission signal between probe sites or groups of probe sites, all of these noise sources can be effectively reduced or eliminated. This occurs because these noise sources are uncorellated to the ADD or SUBTRACT cycles. The noise energy therefore equally contributes to any two integration periods of the same duration. Subtracting the data from any two such periods also subtracts the noise. Since the spatial light modulator is a random access (non-scanning) device, individual probe sites or combinations of probe sites can be analyzed in any order. In a preferred embodiment of the present invention, special "reference" sites 104 are placed on the array. These reference sites are used to subtract noise as mentioned above. The reference sites are basically empty sites and have no hybridization potential. A number of these sites can be placed on the array, and each integration of emission from a hybridization probe site 103 may involve a subsequent subtraction of a "reference" site. When groups of hybridization probe sites are interrogated, an equal number of reference sites from anywhere on the array may be subsequently interrogated (and subtracted) for the purpose of reducing noise.

This signal processing arrangement is very flexible, as it is controlled by software instruction. This capability is supported by all of the analyzer embodiments disclosed herein. Aside from reducing noise, the ability to compare the emission levels of arbitrary groupings of probe sites facilitates experimental design. Useful information involving large numbers of probes can be extracted from microarray experiments in terms of collections of single comparative results (as opposed to large amounts of image data which must be processed using conventional methods). A number of useful types of comparisons can be made (as described in the summary of the invention).

Those skilled in the art will appreciate other types of circuitry that may be employed to perform the basic functions described above. For example, in some embodiments, op-amp integrators may be employed for signal integration.

Additionally, analog transmission gates may be arranged to dump charge from an integration capacitor to provide the RESET function. Subtraction with an analog system may be performed in a number of ways; for example, two analog integrators could be used to alternately integrate during periods of addition and subtraction, the two integrator outputs are then compared with a difference amplifier. With an analog system, a sample-and-hold amplifier provides the SAMPLE function while an analog to digital converter is used to convert the analog signals to a digital format for further processing by the CPU 60.

As mentioned in the summary, in preferred embodiments, combinations of comparisons may be performed by the present invention. One type of combinational comparative measurement entails the repeated comparison between two probe sites or sets of probe sites for the purpose of increasing the Signal-to-Noise Ratio (SNR). This method is applicable to all of the described embodiments, whether the embodiment employs an emission mask, an excitation mask, or a combination excitation/emission mask. In some embodiments, the technique relies on repetitively alternating the spatial light modulator between two interrogation states, while synchronously switching the phase of the detected signal and then averaging it. One of these interrogation states may, for example, be a spatial light modulator pattern that corresponds to one or more hybridization probe sites, while the alternate pattern corresponds to an equal number of reference probe sites. In certain embodiments, comparison is also possible between groups of hybridization probe sites or between a group of probe sites (e.g., reference or hybridization) and a "blank" state that addresses none of the probe sites on the array.

One advantage of repetitive comparison to increase the SNR of measurements made with various embodiments of the present invention is illustrated by considering the SNR during comparison between a hybridization probe site and a reference probe site. The signal arising from interrogation of the reference probe site is considered to represent a "background" signal. The signal from interrogation of a hybridization site includes this same background contribution, with additional signal energy due to any hybridization at the site (e.g., fluorescent emission from labeled hybridized molecules). The additional (desired) signal may, in practice, be smaller than the background signal, limiting the SNR for a single comparison. The SNR may be limited for single comparisons because statistical fluctuations in the background signal may be larger than the signal to be extracted, making the desired signal essentially indistinguishable from the fluctuations in the background signal. By making multiple comparisons, the background fluctuations are essentially averaged out, while the desired difference signal is retained. This method is applicable to detector signals that are digital (i.e., photon counts) or analog (i.e., photocurrent) in nature. This method applies to comparisons between groups of probe sites as well. When background is to be subtracted from a group of hybridization probe sites, a similar number of reference probe sites may be selected as the alternate interrogation pattern group. In some embodiments, the reference sites may be selected from regions on the microarray 38 that are near their respective hybridization probe sites to optimize the match between the background signals from each group.

The system shown in, for example, FIG. 5 may be used to illustrate the enhancement to SNR derived from advantageously repeating the acquisition and comparison of signals from two interrogation states. In some embodiments, the system provides the CPU 60 with a digital photon count signal 58 that represents the difference between the detected signal intensities arising from two spatial light modulator interrogation patterns. Assuming that the photon count rate is low enough to prevent pulse pileup with the particular discriminator used (i.e., <<40 Mhz) the SNR of this comparison can be described as follows:

$$SNR = Na/(Na+2Nb)^{1/2}$$

Na=Average number of signal photons counted during excitation pattern "A"

Nb=Average number of "background" photons counted during pattern "A" or pattern "B"

If Nb<<Na then the SNR approaches $(Na)^{1/2}$. If, however, the background signal is relatively high compared to the hybridization signal (Nb>>Na), then the SNR will approach $Na/(2Nb)^{1/2}$. In this case, the SNR of the signal representing the comparison is dominated by the statistical fluctuations in the background signal. By repeating the comparison a number of times and averaging the results using programmed instruction of the CPU 60, the fluctuations in the background are essentially averaged out. Since background signals arising from alternating interrogation patterns are weighted with alternating polarity, their contribution to the average will approach zero if the background signals for each interrogation state are equal. If the comparison is repeated and averaged M times, the SNR increases by a factor of $M^{1/2}$, as the fluctuations in the running average of Nb become less than the averaged Na.

Figure 7:
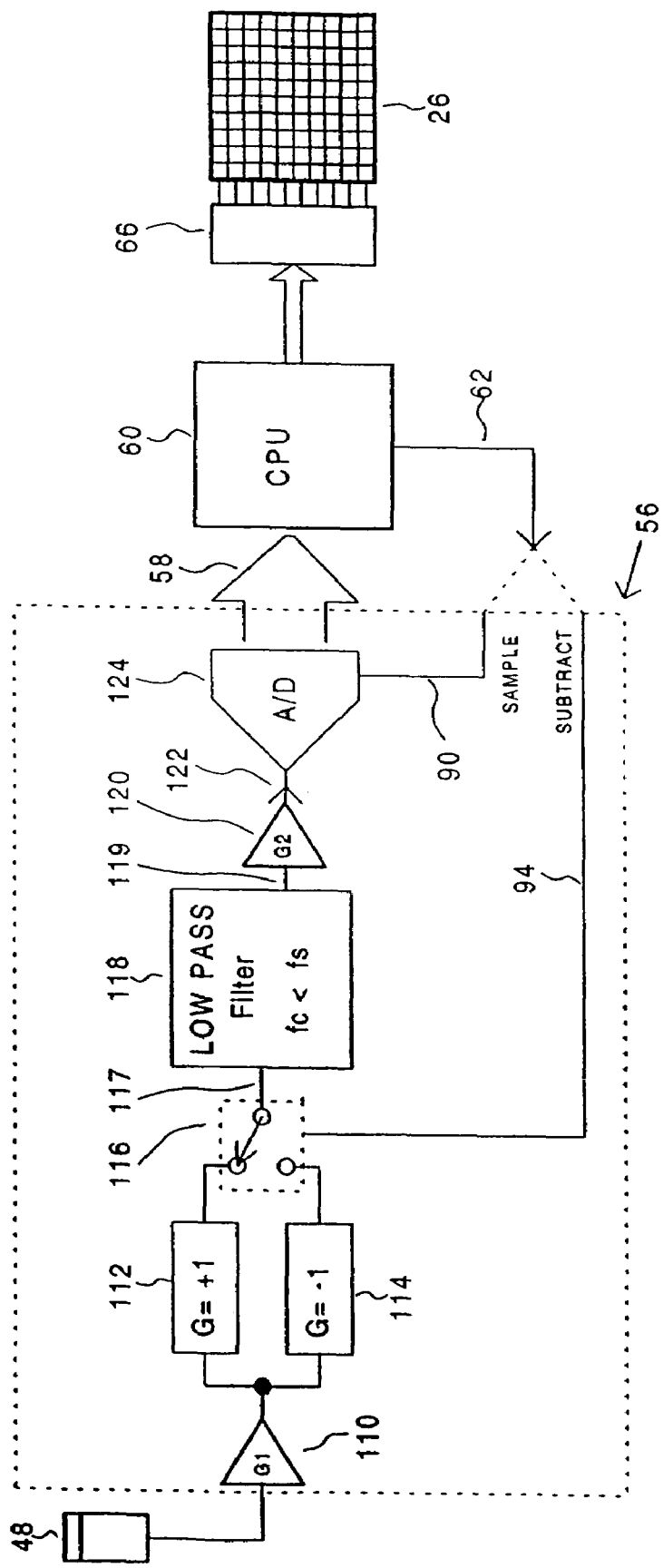
FIG. 7 shows a schematic of a system for reducing signal to noise ratio by repetitive comparison.

Enhancement of SNR by synchronous comparison may also be performed in embodiments where the photodetector is operated in an analog mode. In this mode of operation, a discriminator is not used, and the overlapping current pulses from successive photons produce an average signal intensity (i.e., a photocurrent) that represents the detected light intensity at any particular time. In certain embodiments, this mode of photodetector operation is preferred for higher signal levels, where pulse-pileup may result in non-linearities with the photon counting technique. For example, FIG. 7 shows a block diagram of an analog signal processing arrangement that is suitable for enhancing the SNR of analog signals acquired by photodetectors of the present invention. Those skilled in the art will appreciate the fact that functional blocks 112 through 120 in FIG. 7 may also be implemented as software instructions acting directly on digitized photodetector signals.

Referring to FIG. 7, photodetector 48 (as disclosed herein, or e.g., PE 944, Perkin-Elmer Optoelectronics, Santa Clara, Calif.) generates an analog signal which is smoothed and amplified by gain stage 110. In certain embodiments, where photodetectors 48 produces a photocurrent (e.g., a photomultiplier operated in analog mode), gain stage 110 comprises a transimpedance (current to voltage) amplifier (e.g., Model # A1, Electron Tubes Inc., Rockaway, N.J.). The gain of this stage is selected to prevent saturation with the highest expected levels of signal plus noise. The bandwidth of this stage should be sufficient to pass signal components at the interrogation switching frequency (fs). The maximum interrogation frequency is mainly determined by the dynamic characteristics of the spatial light modulator. In some embodiments, where the spatial light modulator 26 comprises a micromirror array, switching frequencies above 10 KHz are contemplated. Gain blocks 114 and 112 produce inverting and non-inverting representations of the amplified photodetector signal. The gain of these stages are of opposite polarity to provide two alternative multiplicative weights to the detector signal. These gain blocks may be implemented with precision operational amplifiers (e.g., Model # OPA655P, Burr- Brown Inc. Tucson, Ariz.). The CPU 60 controls switching element 116 (e.g., MAX4526, Maxim Integrated Products Inc., Sunnyvale, Calif.) to switch between the inverted and non-inverted versions of the detector signal at the interrogation pattern switching rate (fs). Signal 94 "SUBTRACT" determines the state of the switch 116, and is asserted by CPU 60. Signal 94 is asserted synchronously (in phase) with the CPU's control of the alternating interrogation pattern of the spatial light modulator. Those skilled in the art will appreciate that in some embodiments a two-input multiplier may be substituted for the variable-gain signal path consisting of blocks 112 through 114, provided that signal 94 is level-shifted to provide a balanced positive and negative range for one of the multiplier's inputs. Those skilled in the art will also recognize that in some embodiments said multiplier function may be implemented by directly digitizing the output of amplifier 110 and performing the multiplication using digital calculation by CPU 60 under programmed software control.

Low-pass filter 118 removes switching artifacts from signal 117, and serves to increase the SNR of the comparison by averaging-out statistical fluctuations in the background signal and the signal to be extracted. In some embodiments, the filter 118 is of standard design, preferably having a high-order response (e.g., four or more poles) with low DC error (e.g., MAX280, Maxim Integrated Products Inc., Sunnyvale, Calif.). In other embodiments, the filter 118 is implemented by acquiring a digital representation of signal 117 and calculating a time-averaged result under software control of CPU 60 (e.g., with a running average or Kalman filter algorithm). In some preferred embodiments, the corner frequency (fc) of this filter 118 is chosen to be substantially lower than the interrogation switching frequency (fs), and determines the maximum data-gathering rate of the system. The output signal 119 of filter 118 is a bandwidth-limited representation of the average difference between the photodetector's signal for the two alternating interrogation patterns. Some embodiments of the present invention further comprise an additional DC-coupled gain stage 120 (e.g., Model # PGA203, Burr-Brown Inc. Tucson, Ariz.) that may be used to increase the signal level after filtering. Additionally, in some embodiments, a sampling analog to digital converter 124 (e.g., MAX1200, Maxim Integrated Products Inc., Sunnyvale, Calif.) converts this signal 122 to a digital form for further manipulation or storage by the CPU 60. In preferred embodiments, for each comparative data point to be acquired, sampling and analog to digital conversion may be triggered by the CPU 60 after a number of alternating cycles between interrogation patterns are performed, and the settling time of the low pass filter 118 has elapsed.

FIG. 8 briefly shows the timing relationships between the signals involved in the operation of the signal processing blocks of FIG. 7. Although signals 117 and 119 in FIG. 7 are shown as continuous-time signals, those skilled in the art will appreciate that for embodiments where one or both of these signals are digitally manipulated, FIG. 8 suitably represents their discretely sampled equivalents. In some embodiments of the present invention, for the purpose of illustration, pattern "A" represents an interrogation pattern of hybridization probe sites, while pattern "B" represents an interrogation pattern of reference probe sites. Signal 119 is shown as a flat line to indicate that high frequency components in signal 117 have been removed by low pass filter 118. These high frequency components include, for example, statistical fluctuations in the detector signal as well as the switching frequency (fs) and its harmonics. The small offset of signal 119 is due to the imbalance between the positive and negative heights of signal 117. This height difference is due, for example, to the differences in the amount of hybridization between the alternating interrogation patterns. Signal 119 is therefore a bandwidth-limited representation of the difference between the photodetector signal during each interrogation pattern. To the extent that the magnitudes of the alternating polarity background contributions during alternating interrogation patterns are equal, they are substantially removed from time-averaged signal 119. The present invention contemplates that the removal of the background contribution from signal 119 reduces the possibility of saturation in amplifier 120. In preferred embodiments, this results in higher system sensitivity and dynamic range by allowing the use of a greater gain (G2) for amplifier 120 than would be possible if the background were not removed by the techniques disclosed herein. Those skilled in the art will appreciate that this is also advantageous in embodiments where signal 119 is digitally represented, and amplified using digital multiplicative scaling.

Figure 9:
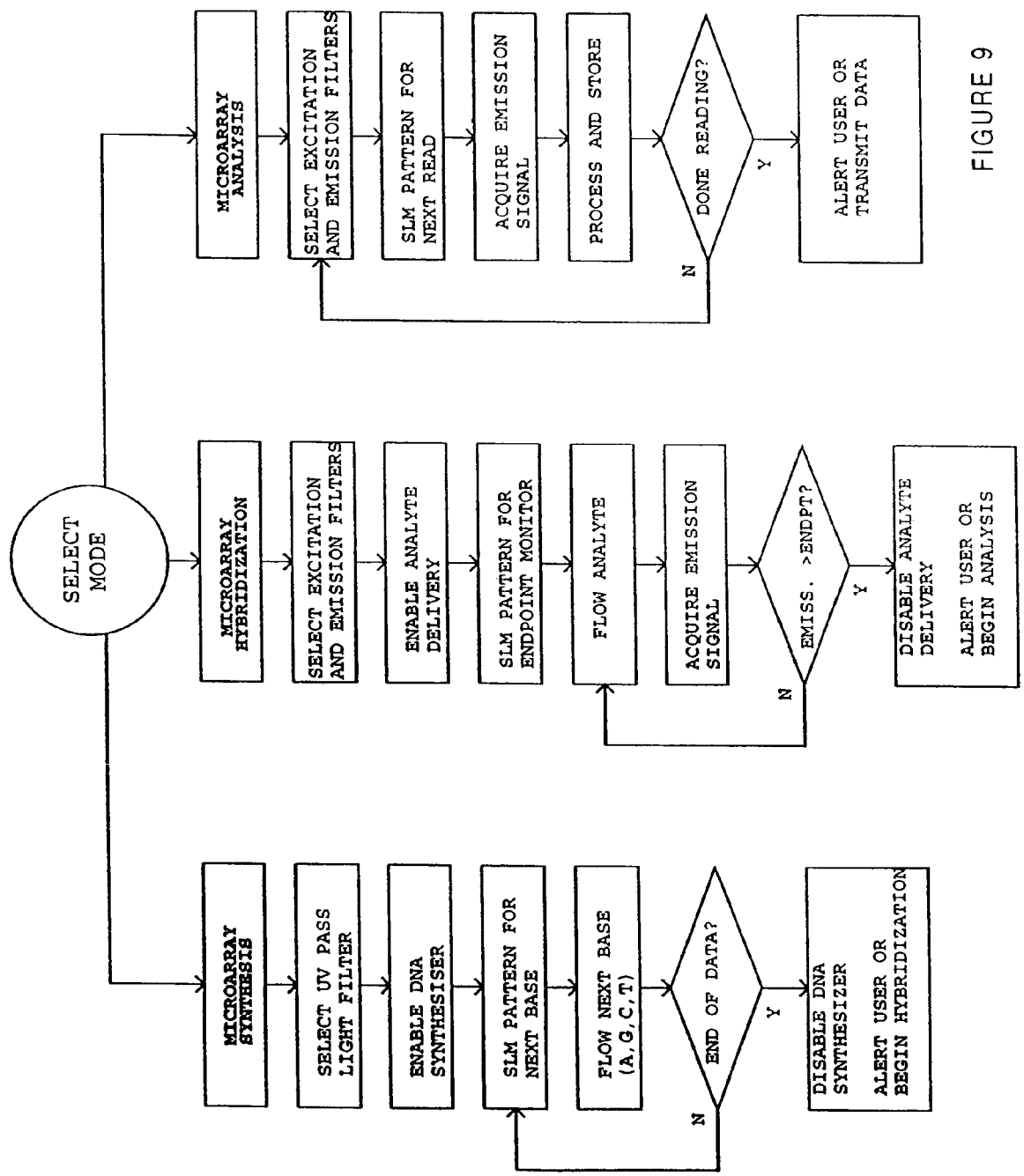
FIG. 9 shows a schematic providing operational modes in some embodiments of the present invention.

Briefly, FIG. 9 depicts the various logic steps employed when the various embodiments of the systems and devices of the present invention are operated in microarray synthesis, microarray hybridization, and microarray detection/analysis modes. While the diagram illustrates synthesis of oligonucleotides, those skilled in the art will appreciate the adaptation of the figure and the present invention to the light-directed synthesis of other types of microarrays. Additionally, those skilled in the art will appreciate that the use of intermediate steps (e.g., reagent purging between exposures) have been omitted from FIG. 9 merely for the sake of clarity.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in electrical engineering, optics, physics, and molecular biology or related fields are intended to be within the scope of the following claims.

I claim:

1. A system comprising a spatial light modulator and detector configured to optically interrogate a microarray, wherein said spatial light modulator comprises a micromirror device, and wherein said system is configured to detect signal at selected locations on said microarray, wherein said signal results from light being directed at said selected locations by said spatial light modulator, and wherein said system is further configured to detect signal at a plurality of reference sites and a plurality of test sites and to calculate a single value for test signal minus reference signal.

2. The system of claim 1, wherein said selected locations comprise biological reaction sites.

3. The system of claim 1, further configured to synthesize molecules using energy directed from said spatial light modulator.

4. The system of claim 1, further comprising means for managing registration of said microarray.

5. The system of claim 1, further comprising a processor configured to measure optical signals detected by said detector.

6. The system of claim 5, further comprising a computer memory capable of storing process data received from said processor.

7. A system comprising a spatial light modulator and detector configured to optically interrogate a microarray, wherein said spatial light modulator comprises a micromirror device, and wherein said system is configured to detect signal at selected locations on said microarray, wherein said signal results from light being directed at said selected locations by said spatial light modulator, and wherein said system is further configured to synthesize molecules using energy directed from said spatial light modulator.

8. The system of claim 7, wherein said selected locations comprise biological reaction sites.

9. The system of claim 7, further comprising means for managing registration of said microarray.

10. The system of claim 7, further comprising a processor configured to measure optical signals detected by said detector.

11. The system of claim 10, further comprising a computer memory capable of storing process data received from said processor.

12. The system of claim 7, wherein said system is further configured to detect signal at a plurality of reference sites and a plurality of test sites and to calculate a single value for test signal minus reference signal.

\* \* \* \* \*